United States Patent
Granchi et al.

(10) Patent No.: US 11,331,146 B2
(45) Date of Patent: May 17, 2022

(54) SYSTEMS AND METHODS FOR GUIDING A USER DURING SURGICAL PLANNING

(71) Applicant: MAKO Surgical Corp., Ft. Lauderdale, FL (US)

(72) Inventors: Carinne Granchi, Weston, FL (US); Jason Otto, Plantation, FL (US); Thomas M. Coon, Redding, CA (US); Michael Ballash, Fort Lauderdale, FL (US); Tamas Erdos, Fort Lauderdale, FL (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 204 days.

(21) Appl. No.: 15/894,461

(22) Filed: Feb. 12, 2018

(65) Prior Publication Data
US 2018/0161105 A1    Jun. 14, 2018

Related U.S. Application Data

(63) Continuation of application No. 14/145,619, filed on Dec. 31, 2013, now Pat. No. 9,888,967.

(60) Provisional application No. 61/747,765, filed on Dec. 31, 2012.

(51) Int. Cl.
| | |
|---|---|
| A61B 34/10 | (2016.01) |
| A61B 34/00 | (2016.01) |
| A61B 34/20 | (2016.01) |
| A61B 34/30 | (2016.01) |

(52) U.S. Cl.
CPC ............. *A61B 34/10* (2016.02); *A61B 34/25* (2016.02); *A61B 34/20* (2016.02); *A61B 34/30* (2016.02); *A61B 2034/104* (2016.02); *A61B 2034/105* (2016.02); *A61B 2034/108* (2016.02)

(58) Field of Classification Search
CPC ...................................................... A61B 19/50
See application file for complete search history.

(56) References Cited

U.S. PATENT DOCUMENTS

| | | | |
|---|---|---|---|
| 5,445,166 A | 8/1995 | Taylor | |
| 5,682,886 A * | 11/1997 | Delp | ................... A61B 17/154 |
| | | | 128/920 |
| 5,824,085 A | 10/1998 | Sahay et al. | |
| 6,112,113 A | 8/2000 | Van Der Brug et al. | |

(Continued)

OTHER PUBLICATIONS

R. H. Taylor et al., "An overview of computer-integrated surgery at the IBM Thomas J. Watson Research Center," in IBM Journal of Research and Development, vol. 40, No. 2, pp. 163-183, Mar. 1996, doi: 10.1147/rd.402.0163. (Year: 1996).*

(Continued)

*Primary Examiner* — William L Bashore
*Assistant Examiner* — Nathan K Shrewsbury
(74) *Attorney, Agent, or Firm* — Foley & Lardner LLP

(57) ABSTRACT

A method for improving the development of an initial surgical plan includes receiving input information, developing an initial surgical plan based upon the input information, and allowing a user to customize the initial surgical plan by providing input related to modifications to the initial surgical plan. The method further includes storing information related to the modifications to the initial surgical plan and using the stored information to develop a subsequent initial surgical plan based on the modifications.

20 Claims, 24 Drawing Sheets

(56) References Cited

U.S. PATENT DOCUMENTS

| | | |
|---|---|---|
| 6,198,794 B1 | 3/2001 | Peshkin et al. |
| 6,285,902 B1 | 9/2001 | Kienzle et al. |
| 6,358,245 B1 | 3/2002 | Edwards et al. |
| 6,450,978 B1 | 9/2002 | Brosseau et al. |
| 6,470,207 B1 | 10/2002 | Simon et al. |
| 6,725,080 B2 | 4/2004 | Melkent et al. |
| 6,969,384 B2 | 11/2005 | De Juan et al. |
| 7,494,189 B2 | 2/2009 | Otto et al. |
| 7,542,791 B2 | 6/2009 | Mire et al. |
| 7,618,421 B2 | 11/2009 | Axelson et al. |
| D622,854 S | 8/2010 | Otto et al. |
| 7,771,436 B2 | 8/2010 | Moctezuma De La Barrera et al. |
| D625,415 S | 10/2010 | Otto et al. |
| D626,234 S | 10/2010 | Otto et al. |
| 7,838,231 B2 | 11/2010 | Hidebrandt et al. |
| 7,842,092 B2 | 11/2010 | Otto et al. |
| 8,010,180 B2 | 8/2011 | Quaid et al. |
| 8,282,167 B2 | 10/2012 | Kirubaharan et al. |
| 8,382,765 B2 * | 2/2013 | Axelson ................. A61B 34/10 606/88 |
| 8,475,535 B2 | 7/2013 | Otto |
| D692,916 S | 11/2013 | Granchi et al. |
| 9,424,656 B2 * | 8/2016 | Luo ........................ A61B 34/10 |
| 9,913,691 B2 * | 3/2018 | Brooks ................. A61B 34/10 |
| 2003/0009354 A1 * | 1/2003 | Arbogast ............... G16H 40/67 705/2 |
| 2003/0055679 A1 | 3/2003 | Soll et al. |
| 2004/0015070 A1 | 1/2004 | Liang et al. |
| 2004/0068187 A1 | 4/2004 | Krause et al. |
| 2004/0102866 A1 | 5/2004 | Harris et al. |
| 2004/0169673 A1 | 9/2004 | Crampe et al. |
| 2005/0059873 A1 | 3/2005 | Glozman et al. |
| 2007/0023180 A1 | 2/2007 | Komarek et al. |
| 2007/0066917 A1 | 3/2007 | Hodorek et al. |
| 2007/0078678 A1 * | 4/2007 | DiSilvestro ............ A61B 34/20 705/2 |
| 2007/0080237 A1 | 4/2007 | Burk et al. |
| 2007/0082538 A1 | 4/2007 | Hegner et al. |
| 2007/0129626 A1 * | 6/2007 | Mahesh .................. A61B 34/76 600/407 |
| 2007/0208234 A1 * | 9/2007 | Bhandarkar ........... A61B 90/36 600/300 |
| 2008/0004517 A1 * | 1/2008 | Bhandarkar .............. G06T 7/33 600/407 |
| 2008/0058945 A1 | 3/2008 | Hajaj et al. |
| 2008/0081982 A1 | 4/2008 | Simon et al. |
| 2008/0262812 A1 | 10/2008 | Arata et al. |
| 2009/0043556 A1 | 2/2009 | Axelson et al. |
| 2009/0089081 A1 | 4/2009 | Haddad |
| 2009/0093712 A1 * | 4/2009 | Busch .................... A61B 6/032 600/424 |
| 2009/0171203 A1 | 7/2009 | Avital et al. |
| 2009/0254367 A1 | 10/2009 | Delcher et al. |
| 2010/0069919 A1 | 3/2010 | Carls et al. |
| 2010/0086186 A1 | 4/2010 | Zug et al. |
| 2010/0094429 A1 | 4/2010 | Otto |
| 2010/0153076 A1 | 6/2010 | Bellettre et al. |
| 2010/0153081 A1 | 6/2010 | Bellettre et al. |
| 2010/0217336 A1 | 8/2010 | Crawford et al. |
| 2010/0217400 A1 | 8/2010 | Nortman et al. |
| 2010/0312094 A1 | 12/2010 | Guttman et al. |
| 2010/0324692 A1 | 12/2010 | Uthgenannt et al. |
| 2011/0092804 A1 | 4/2011 | Schoenefeld et al. |
| 2011/0166886 A1 | 7/2011 | Zeringue et al. |
| 2012/0016690 A1 * | 1/2012 | Ramarajan ............. G16H 15/00 705/2 |
| 2012/0035464 A1 | 2/2012 | Raju et al. |
| 2012/0078254 A1 | 3/2012 | Ashby et al. |
| 2012/0078831 A1 | 3/2012 | Newcott |
| 2012/0310617 A1 | 12/2012 | Bellettre et al. |
| 2013/0169423 A1 | 7/2013 | Iorgulescu et al. |
| 2013/0172783 A1 | 7/2013 | Ikits et al. |
| 2013/0173008 A1 | 7/2013 | Bechtold et al. |
| 2013/0173010 A1 | 7/2013 | Irwin et al. |
| 2013/0211792 A1 | 8/2013 | Kang et al. |
| 2013/0304429 A1 | 11/2013 | Haimerl |
| 2013/0317344 A1 | 11/2013 | Borus et al. |
| 2014/0081659 A1 | 3/2014 | Nawana et al. |
| 2014/0180290 A1 | 6/2014 | Otto et al. |
| 2014/0188134 A1 | 7/2014 | Nortman et al. |
| 2014/0189508 A1 * | 7/2014 | Granchi ................. A61B 34/10 715/705 |
| 2018/0373416 A1 * | 12/2018 | Nikou .................... A61B 34/10 |

OTHER PUBLICATIONS

U.S. Appl. No. 29/329,712, filed Dec. 19, 2008, Otto.
U.S. Appl. No. 29/329,715, filed Dec. 19, 2008, Otto.
U.S. Appl. No. 29/466,144, filed Sep. 4, 2013, Mako Surgical Corp.
U.S. Appl. No. 29/466,147, filed Sep. 4, 2013, Mako Surgical Corp.
U.S. Appl. No. 29/466,148, filed Sep. 4, 2013, Mako Surgical Corp.

* cited by examiner

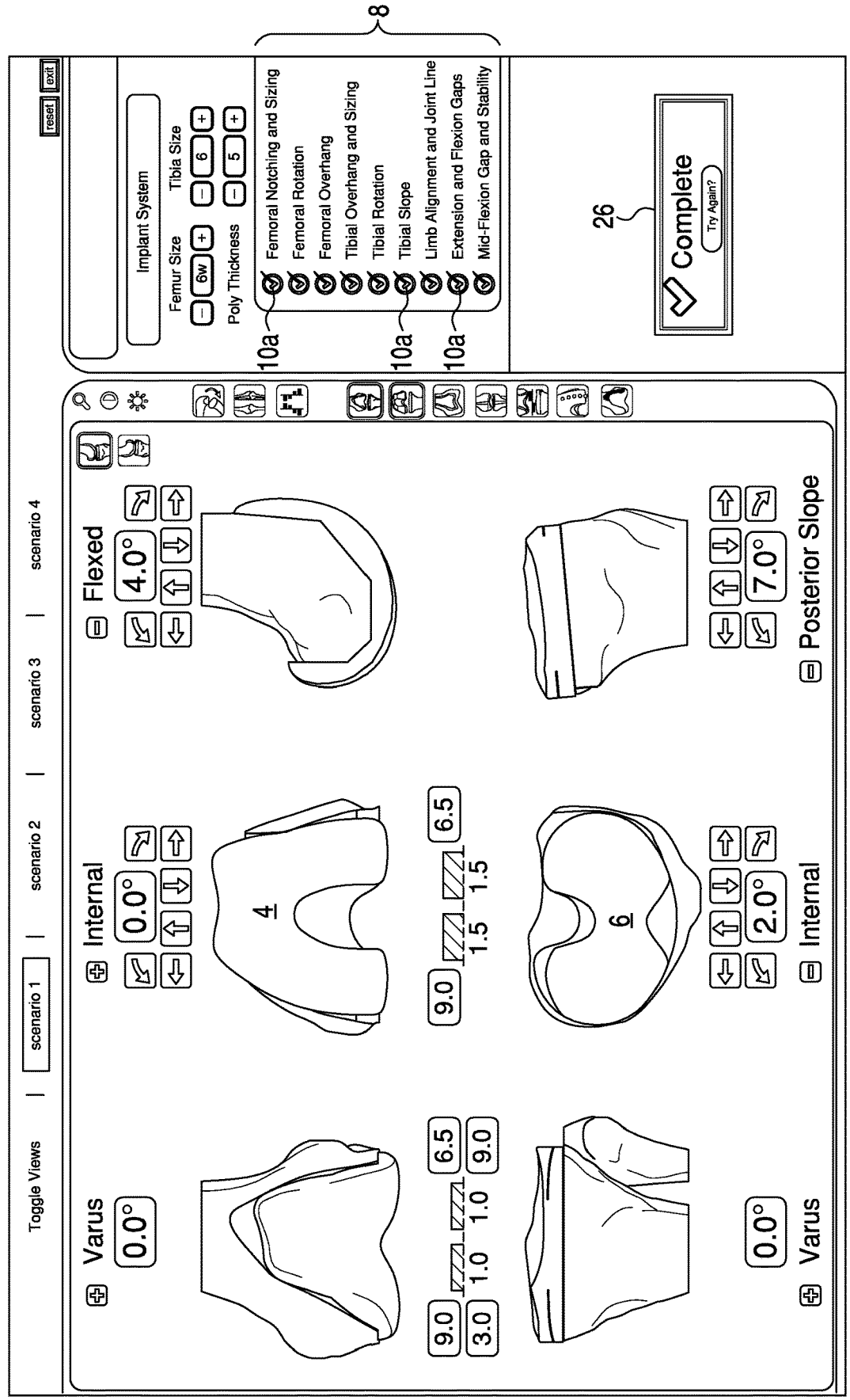

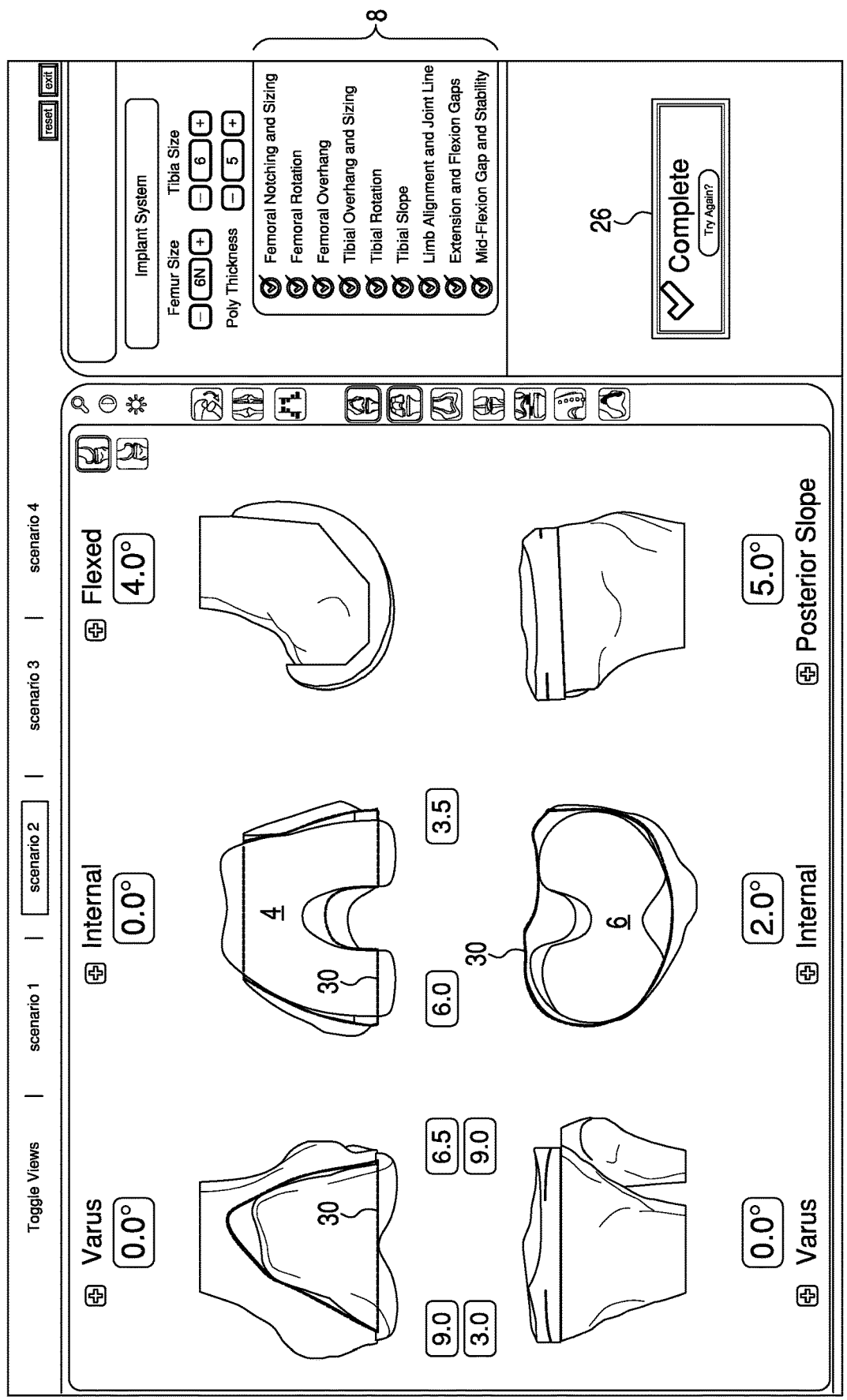

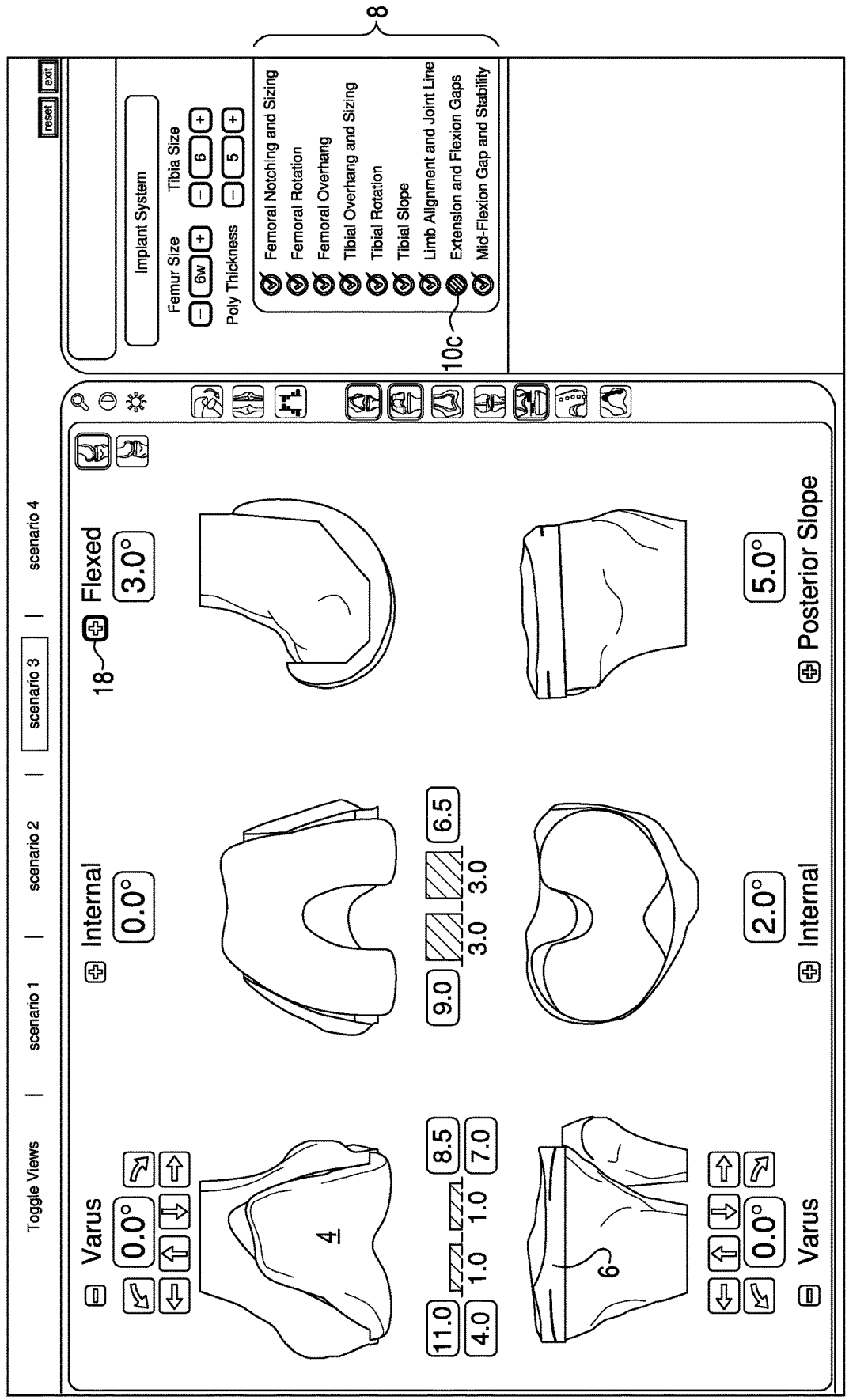

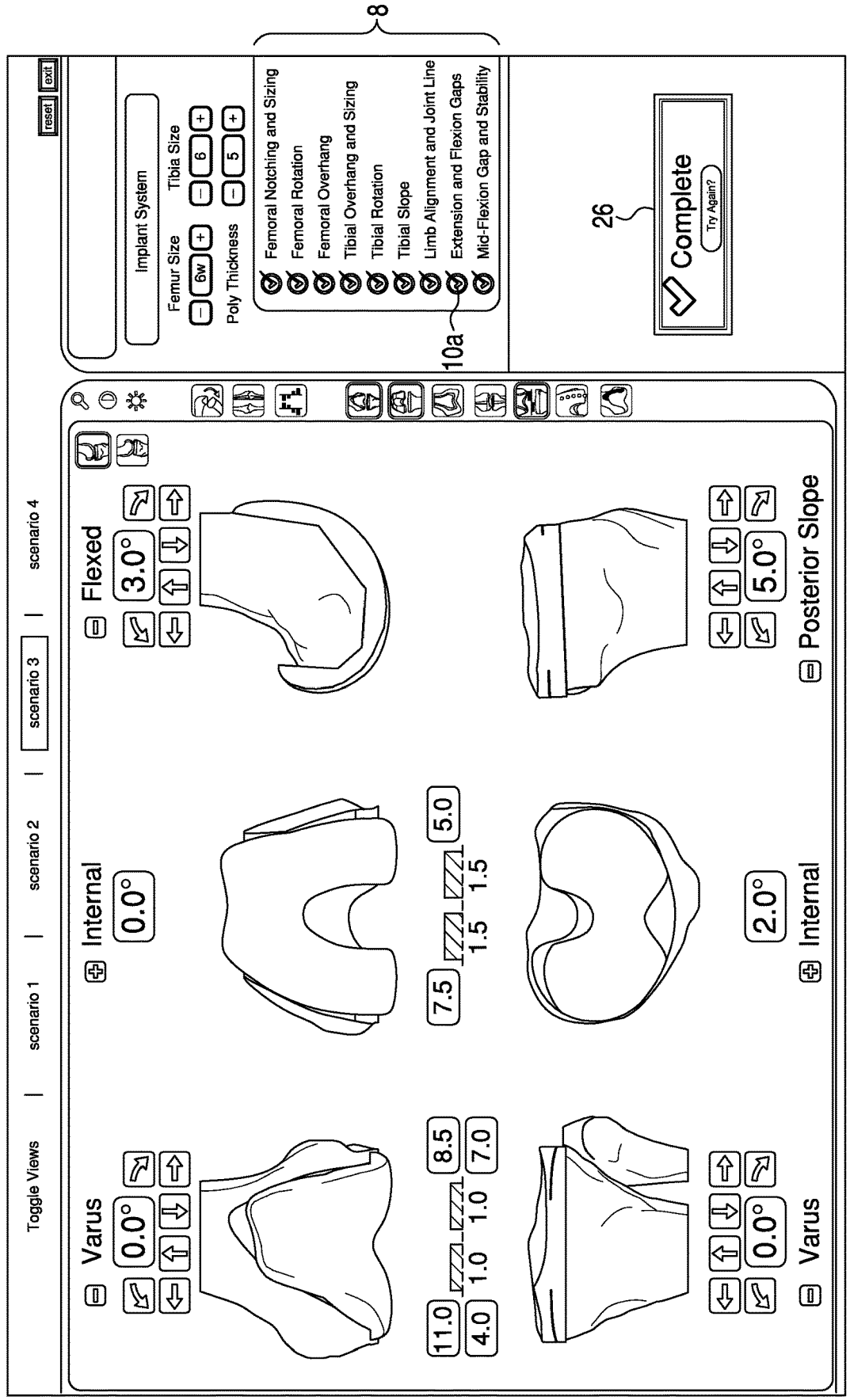

SYSTEMS AND METHODS FOR GUIDING A USER DURING SURGICAL PLANNING

CROSS-REFERENCE TO RELATED PATENT APPLICATION

This application is a continuation of U.S. patent application Ser. No. 14/145,619, filed Dec. 31, 2013, which claims the benefit of and priority to U.S. Provisional Patent Application No. 61/747,765, filed Dec. 31, 2012, each of which is incorporated by reference herein in its entirety.

BACKGROUND

The present invention relates generally to surgical planning in connection with computer-assisted surgeries. More particularly, the embodiments described herein relate to the interactions between a user and an interface of a surgical planning system.

Planning systems for computer-assisted surgical systems produce surgical plans based on input information. To develop the surgical plan, the planning system applies an algorithm to the input information. For example, during planning of a total knee arthroplasty, input information may include information related to the patient's bone structure and other physical characteristics. The surgical plan developed by the planning system shows where any implants, such as a femoral component and a tibial component, should be placed.

After the surgical plan has been produced, the user (e.g., a surgeon, other medical practitioner, or a technical specialist) can customize the plan based on the user's additional knowledge. However, in conventional planning systems, the user may not know how the planning system arrived at the surgical plan. In other words, the user does not understand the algorithm applied to the input information to develop the surgical plan. A lack of knowledge related to the underlying algorithm used by the planning system may make it more difficult for the user to effectively modify the surgical plan (e.g., the planned implant placement or other specifics related to the surgical plan).

SUMMARY

The methods described herein guide a user during surgical planning in a manner that provides the user with information related to an initial surgical plan, thereby improving the transparency of the planning system relative to conventional planning systems. In addition, the methods for guiding a user described herein allow the user to customize the initially developed surgical plan.

In accordance with one aspect, the present disclosure relates to a method for guiding a user during surgical planning. The method includes receiving input information; developing an initial surgical plan based upon the input information; and guiding a user by providing suggested actions to the user. If the user performs the suggested actions, the suggested actions lead the user to the initial surgical plan. The method further includes providing the user with an option to deviate from one or more of the suggested actions by performing non-suggested actions, wherein deviation from one or more of the suggested actions leads to development of a final surgical plan that is different from the initial surgical plan.

According to another aspect, the present disclosure relates to a system for guiding a user during surgical planning. The system includes a processing circuit configured to receive input information; apply an algorithm to the input information to develop an initial surgical plan; and display on a display device a plurality of icons in sequence, each of the plurality of icons having a distinguishing characteristic configured to alert the user to select each of the plurality of icons. If the user selects each of the plurality of icons having a distinguishing characteristic, the selections lead the user to the initial surgical plan. The processing circuit is further configured to customize the initial surgical plan to create a final surgical plan upon user selection of a displayed icon without a distinguishing characteristic.

The invention is capable of other embodiments and of being practiced or being carried out in various ways. Alternative exemplary embodiments relate to other features and combinations of features as may be generally recited in the claims.

BRIEF DESCRIPTION OF THE FIGURES

The invention will become more fully understood from the following detailed description, taken in conjunction with the accompanying drawings, wherein like reference numerals refer to like elements, in which:

FIG. 1F is a representation of a display screen after completion of guiding a user during surgical planning according to the first exemplary embodiment.

FIG. 2C is a representation of a display screen after completion of guiding a user during surgical planning according to the second exemplary embodiment.

FIG. 3E is a representation of a display screen during a fifth step of guiding a user during surgical planning according to the third exemplary embodiment.

FIG. 3G is a representation of a display screen after completion of guiding a user during surgical planning according to the third exemplary embodiment.

DETAILED DESCRIPTION

Figure 1A:
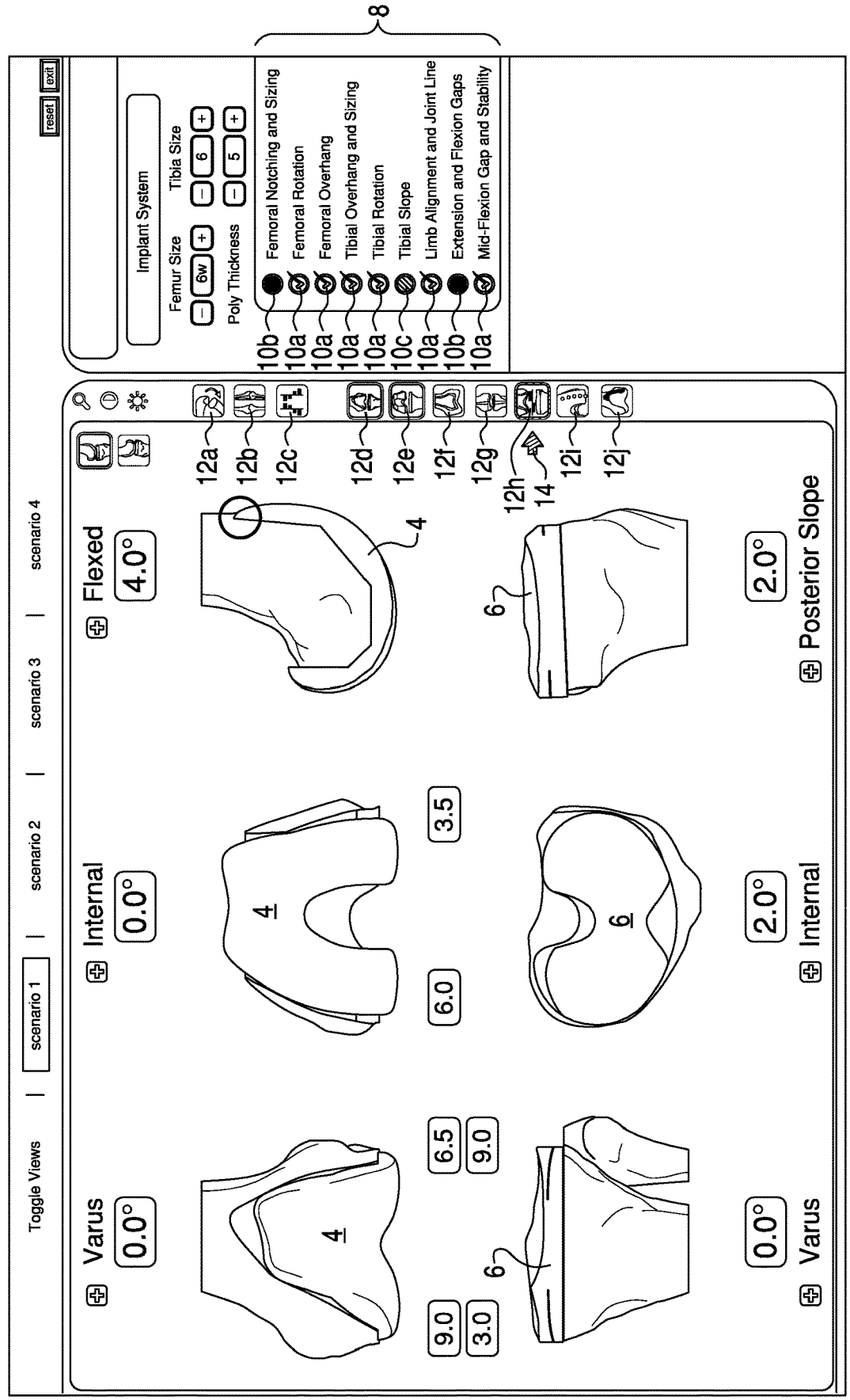
FIG. 1A is a representation of a display screen during a first step of guiding a user during surgical planning according to a first exemplary embodiment.

Before turning to the figures, which illustrate the exemplary embodiments in detail, it should be understood that the application is not limited to the details or methodology set forth in the description or illustrated in the figures. It should also be understood that the terminology is for the purpose of description only and should not be regarded as limiting.

FIGS. 1A-4F provide various representations of a user display during different exemplary embodiments described herein. In each of the exemplary embodiments, input information has been received (e.g., by a surgical planning system) and an algorithm has been applied to the input information to develop an initial surgical plan. Input information may relate to the patient's bone structure or other physical characteristics. Imaging techniques, such as CT, MRI, or ultrasound, may be used to obtain three-dimensional representations of the patient's anatomy, such as the representations of the femur and tibia shown in FIGS. 1A-4F. General surgical planning and navigation, including haptic control and feedback, may be performed by a computerized surgical system such as that depicted in FIGS. 5 and 6 (and described below), and as described in U.S. Pat. No. 8,010,180 "Haptic Guidance System and Method" to Quaid et al., which is incorporated herein by reference in its entirety.

FIGS. 1A-4F provide examples of guiding a user during surgical planning by providing a plurality of suggested actions to the user. The user is guided via a display screen, shown in various exemplary embodiments as graphical user interface (GUI) 2, to perform the suggested actions. The suggested actions may correspond to steps of an algorithm used by a planning system to develop an initial surgical plan. Guiding a user in this manner allows the user to 1) learn how the initial surgical plan was developed by the planning system, and 2) customize the initial surgical plan during the user-guidance process. If the user performs the suggested actions, the suggested actions will lead the user to the initial surgical plan. However, the user has the option to deviate from one or more of the suggested actions by performing non-suggested actions. Deviation from one or more of the suggested actions leads to development of a final surgical plan that is different from the initial surgical plan.

In connection with guiding a user, the GUI 2 illustrated in FIGS. 1A-4F may display a series of icons in sequence, each of the icons having a distinguishing characteristic intended to alert the user to select the icons. If the user selects the icons having a distinguishing characteristic, the selections will lead the user to the initial surgical plan. However, the user can customize the initial surgical plan by selecting a displayed icon without a distinguishing characteristic.

In accordance with one embodiment, GUI 2 provides virtual representations of a femoral component 4 and a tibial component 6 on virtual models of a patient's femur and tibia, respectively. References herein to femoral component 4 and tibial component 6 are understood to be references to the virtual representations of these components as shown on a GUI 2.

The GUI 2 also displays criteria in the form of a list 8. The criteria are related to the surgical plan shown on the current display of GUI 2. Each of the criteria is associated with one or more acceptable values. Acceptable values for any particular criterion may be values below a maximum threshold, above a minimum threshold, or within a predefined range. Some examples of displayed criteria, as can be seen in FIGS. 1A-4F, include femoral notching and sizing, femoral rotation, femoral overhang, tibial overhang and sizing, tibial rotation, tibial slope, limb alignment and joint line, extension and flexion gaps, and mid-flexion gap and stability. These criteria relate to surgical planning of a total knee arthroplasty (the example used in the exemplary embodiments of FIGS. 1A-4F). However, the criteria may be chosen to be applicable to any planned surgical procedure.

Each of the criteria in list 8 includes a corresponding indicator 10 configured to provide the user with information related to the particular criterion. The information provided by indicator 10 may relate to whether the corresponding criterion has an acceptable value. The indicators 10 may be circular images configured to provide information via a display feature. Each indicator 10 may be configured to change its display feature to convey information. In one embodiment, if a certain criterion has an acceptable value during a stage of user-guidance, the corresponding indicator indicates acceptability by displaying a first display feature, such as a checkmark. For example, in FIG. 1A, femoral overhang and several other criteria have acceptable values and are therefore marked with an indicator 10a having a first display feature (e.g., a checkmark). However, if a certain criterion does not have an acceptable value during a stage of user-guidance, the corresponding indicator will display a second display feature, such as being filled in. In FIG. 1A, the femoral notching and sizing criterion and the extension and flexion gaps criterion do not have acceptable values. These criteria are therefore marked with a indicator 10b having a second display feature (e.g., a filled interior). Criteria that are within a predefined range of an acceptable value may be marked with an indicator having a third display feature, such as a shaded interior. In FIG. 1A, the tibial slope criteria is within a predefined range of an acceptable value, so the indicator 10c associated with tibial slope has a shaded interior. Thus, the indicators 10a, 10b, and 10c can provide information related to the current values of the criteria in list 8 by displaying different features. Any type of display features may be utilized to convey information to a user.

In one embodiment, the indicators 10 provide information related to changes in the values of the criteria in list 8 by changing color in connection with changes to the criteria values. Thus, the first, second, and third display features can be different colors. The indicators 10 may change color when the user performs suggested or non-suggested actions that change one or more of the criteria. A change of a criterion value may be, for example, a change from an unacceptable value to a value within a certain range of an acceptable value. The corresponding indicator indicates this change by changing from an indicator 10*b* having a second color (e.g., red) to an indicator 10*c* having a third color (e.g., yellow). Alternatively, a change in criterion value may be a change from a value within a certain range of an acceptable value to an acceptable value. The corresponding indicator indicates this change by changing from an indicator 10*c* having a third color (e.g., yellow) to an indicator 10*a* a having a first color (e.g., green).

GUI 2 further includes a plurality of icons 12*a*-12*j*. A user may select (e.g., touch, mouse click, etc.) the icons to cause additional information to be displayed. Various types of information that may be displayed to a user include or relate to: 3D flex pose capture (icon 12*a*), limb alignment (icon 12*b*), gap graphs (icons 12*c* and 12*h*), virtual models of implants (icon 12*d*), planned bone resections (icon 12*e*), CT scan overlay (icon 12*f*), alignment axes (icon 12*g*), trace points (icon 12*i*) and over/under hang (icon 12*j*).

Figure 1B:
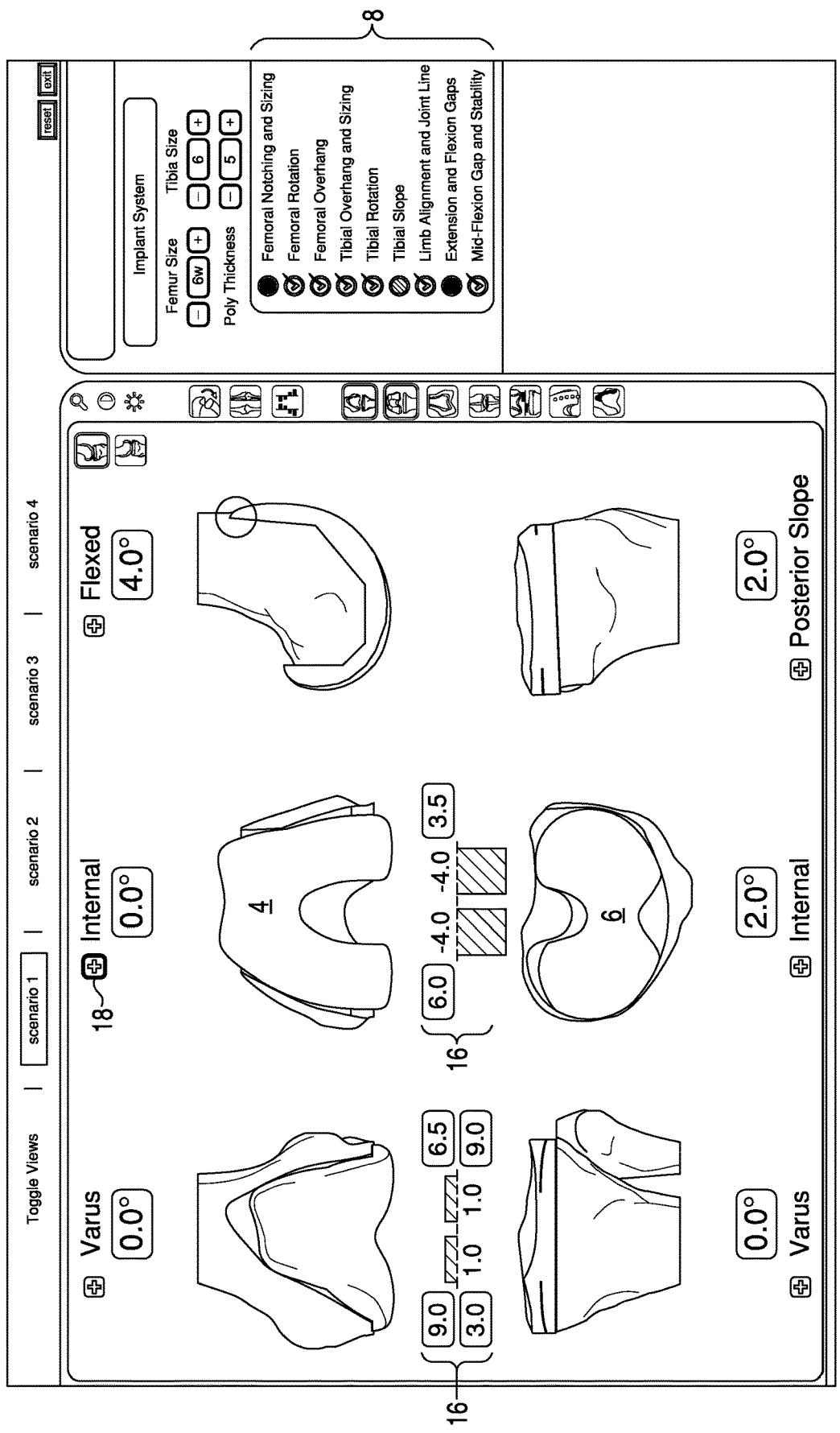
FIG. 1B is a representation of a display screen during a second step of guiding a user during surgical planning according to the first exemplary embodiment.
Figure 1C:
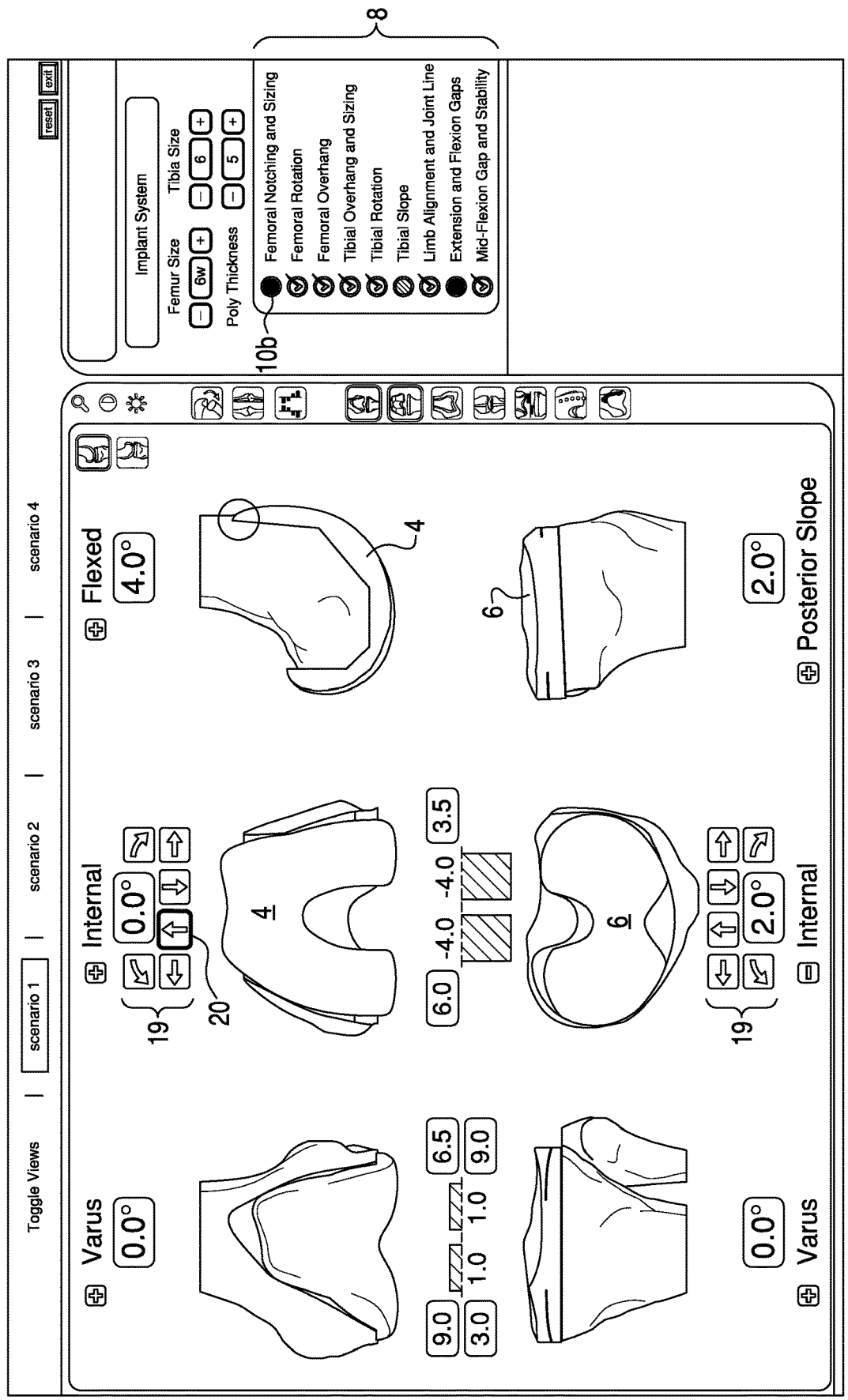
FIG. 1C is a representation of a display screen during a third step of guiding a user during surgical planning according to the first exemplary embodiment.

FIGS. 1A-1F illustrate a first exemplary embodiment for guiding a user during surgical planning. In the embodiment of FIGS. 1A-1F, the user is guided through steps relating to planning the placement of femoral and tibial components for a total knee arthroplasty. Referring to FIG. 1A, a GUI 2 during a first step of guiding a user is shown. The GUI 2 provides a first suggested action to a user by displaying an icon having a distinguishing characteristic. The distinguishing characteristic is configured to alert the user to select the icon. In FIG. 1A, icon 12*h* is marked with two distinguishing characteristics—an outline and a guiding arrow 14. The outline may be shown in a specific color (e.g., pink), and the guiding arrow 14 may be shown in the same or different color. The distinguishing characteristic of icon 12*h* guides the user to select the icon 12*h*. Selecting the icon 12*h* causes additional information related to gaps between femoral component 4 and tibial component 6 to be displayed in the form of bar graphs 16, as shown in FIG. 1B. FIG. 1B illustrates GUI 2 during a second step of guiding a user during surgical planning. In FIG. 1B, an expansion box 18 includes a distinguishing characteristic (e.g., an outline in a specific color) to guide the user to select the expansion box 18. Selecting the expansion box 18 causes placement arrows 19 to appear, as shown in FIG. 1C.

The GUI 2 next guides the user by suggesting how to adjust the placements of the femoral component 4 and tibial component 6 to achieve acceptable criteria values. The suggested action of FIG. 1C is selecting an icon to cause a change in placement of a virtual implant (in this step, the femoral component 4). The marked arrow 20 shown in FIG. 1C includes a distinguishing characteristic (e.g., an outline in a specific color) to guide the user to select the marked arrow 20. When the user selects the marked arrow 20, the placement of femoral component 4 shifts from the placement shown in FIG. 1C to the placement shown in FIG. 1D.

Figure 1D:
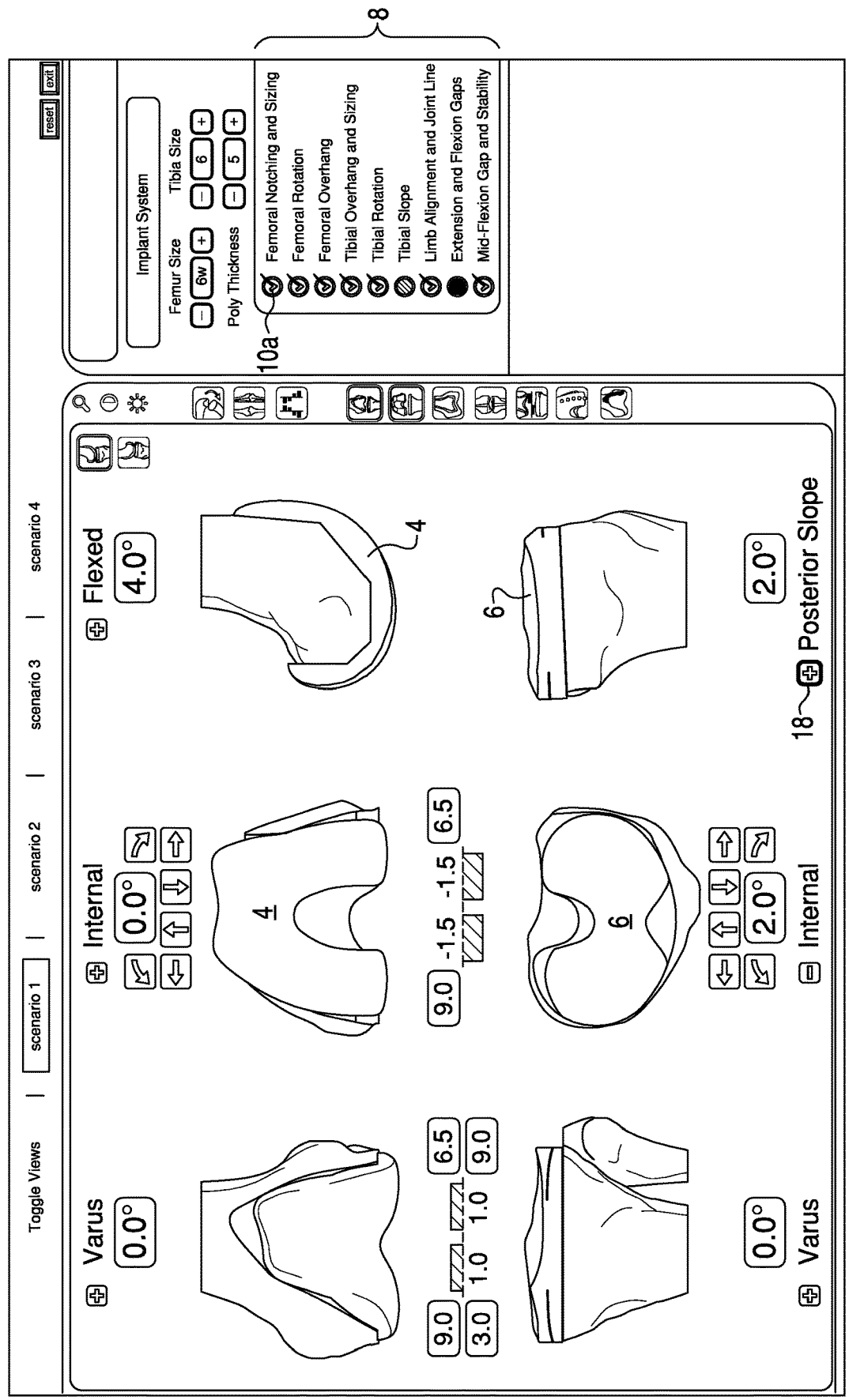
FIG. 1D is a representation of a display screen during a fourth step of guiding a user during surgical planning according to the first exemplary embodiment.

As can be seen in FIG. 1D, the shift of femoral component 4 caused the femoral notching and sizing criterion to have an acceptable value. To provide this information to the user, the femoral notching and sizing criterion in FIG. 1D is marked with an indicator 10*a* having a checkmark (in contrast, a filled-in indicator 10*b* corresponded to femoral notching and sizing in FIG. 1C). Colors may also be used in the relevant indicators to provide this information. The user can therefore see a direct cause and effect between shifting the placement of femoral component 4 and the femoral notching and sizing criterion having an acceptable value.

Figure 1E:
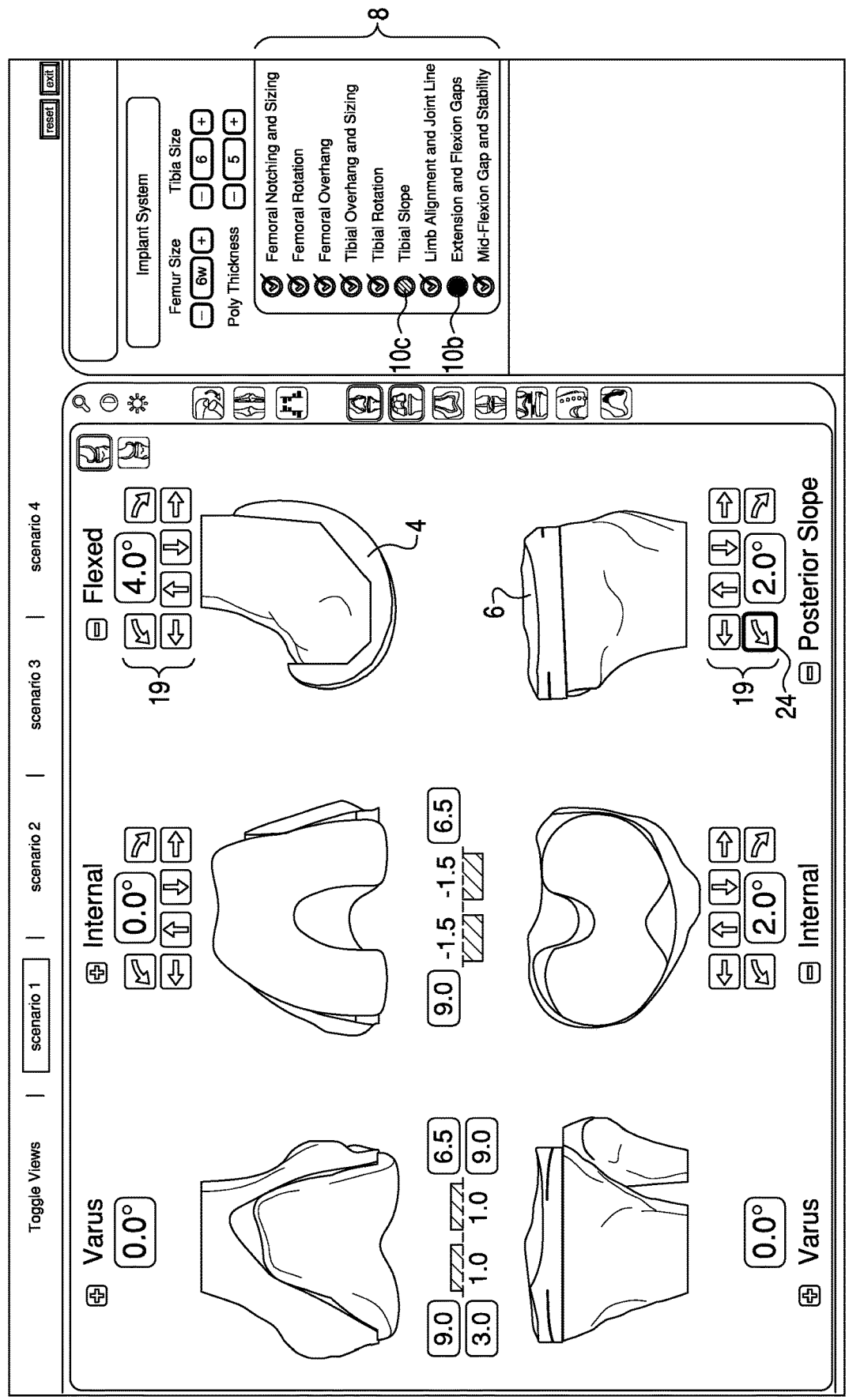
FIG. 1E is a representation of a display screen during a fifth step of guiding a user during surgical planning according to the first exemplary embodiment.

In FIG. 1D, expansion box 18 includes a distinguishing characteristic (e.g., an outline in a specific color) to guide the user to select expansion box 18. Selecting expansion box 18 causes placement arrows 19 to appear as shown in FIG. 1E, allowing the user to adjust the placement of a virtual implant (in this step, tibial component 6). The user is guided to adjust the posterior slope of the tibial component 6 by selecting marked arrow 24, which includes a distinguishing characteristic. Selecting marked arrow 24 adjusts the tibial component 6 to the placement shown in FIG. 1F. The change in placement or orientation may be accomplished incrementally via several selections of arrow 24. As shown in FIG. 1F, this adjustment to the posterior slope (e.g., from 2.0° to 7.0°) caused both the tibial slope criterion and extension and flexion gaps criterion to have acceptable values, as shown by their associated checked indicators 10*a*. The GUI 2 indicates that the planning of femoral and tibial component placement is complete by displaying a completion icon 26.

The actions suggested to the user (e.g., selecting marked arrows 20 or 24) are presented in a predetermined manner. If the user performs each suggested action of FIGS. 1A-1F (e.g., selects each of the plurality of icons having a distinguishing characteristic), the actions will lead the user to the initial surgical plan developed by applying an algorithm to input information. Thus, via GUI 2, the user is guided through steps that, if followed, would lead the user to the initially developed surgical plan. This guidance illustrates to the user how the algorithm was applied to arrive at the initial surgical plan. The user guidance therefore provides transparency into how the initial surgical plan was developed.

However, the user has the option to deviate from one or more of the suggested actions by performing non-suggested actions, such as selecting a displayed icon without a distinguishing characteristic. Deviation from one or more of the plurality of suggested actions may lead to the development of a final surgical plan that is different from the initial surgical plan. In this manner, the user can customize the initial surgical plan to create a final surgical plan. The final surgical plan can differ from the initial surgical plan in one or more ways, such as in placement of a virtual implant, type of virtual implant, or size of virtual implant. For example, in the step shown by the GUI 2 in FIG. 1C, one way the user can customize the initial surgical plan is by selecting the arrows surrounding marked arrow 20, which do not have distinguishing characteristics. Selecting an arrow other than marked arrow 20 would customize the surgical plan by causing the femoral component 4 to shift to a different placement than the placement shown in FIG. 1D (which resulted from selecting marked arrow 20). The user guidance therefore allows the user to customize the initial plan in a straightforward and intuitive manner.

Figure 2A:
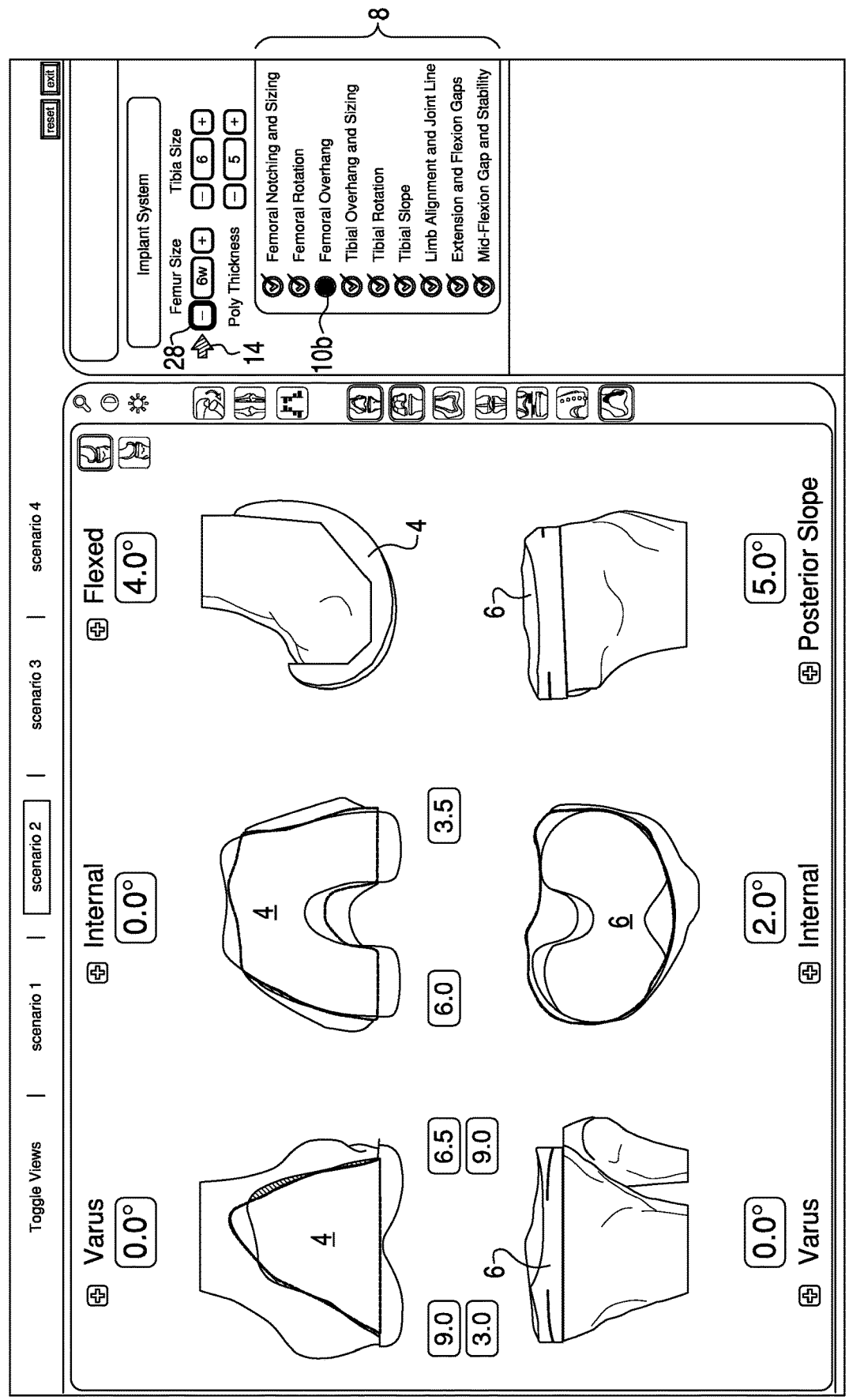
FIG. 2A is a representation of a display screen during a first step of guiding a user during surgical planning according to a second exemplary embodiment.
Figure 2B:
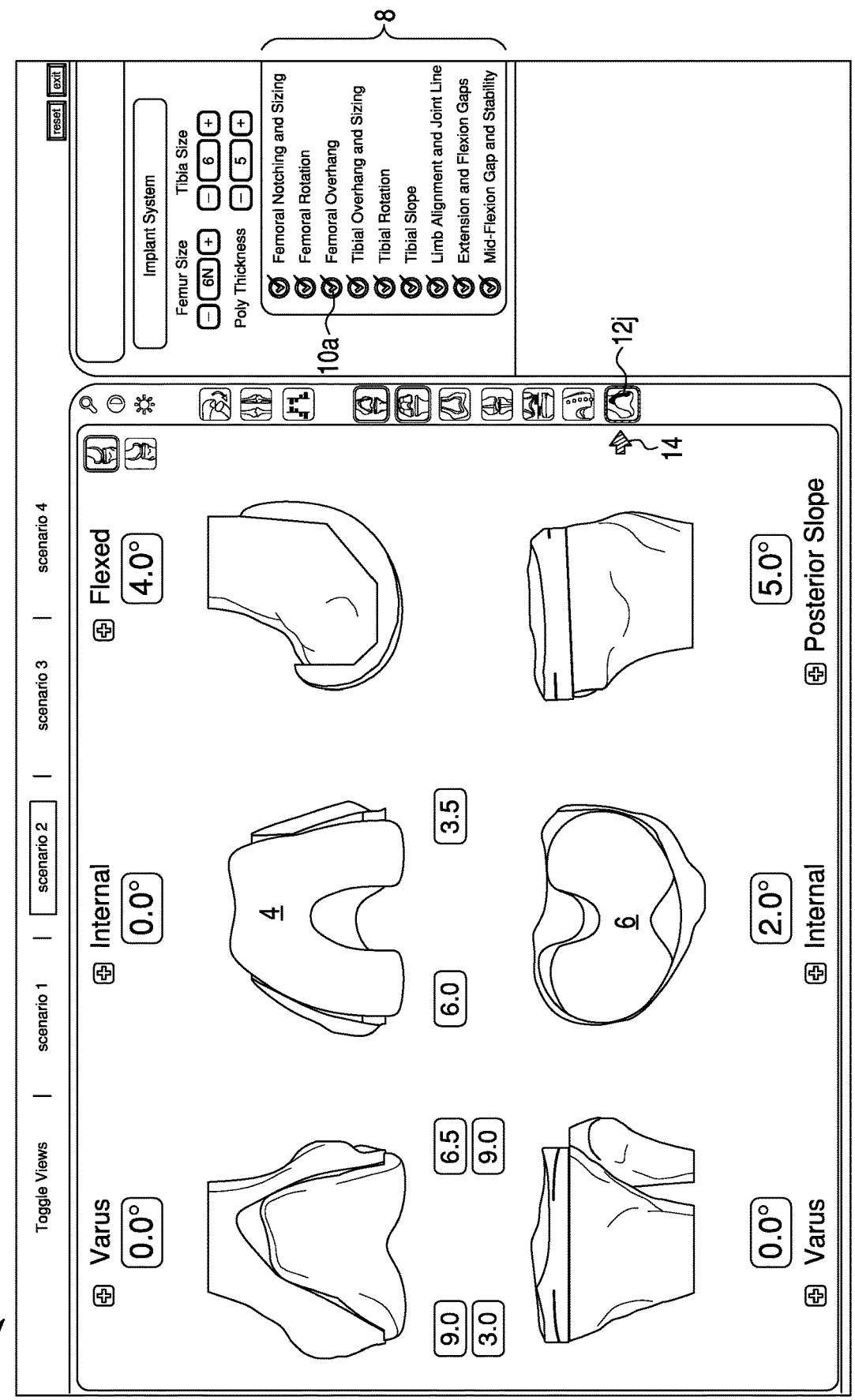
FIG. 2B is a representation of a display screen during a second step of guiding a user during surgical planning according to the second exemplary embodiment.

FIGS. 2A-2C illustrate a second exemplary embodiment for guiding a user during surgical planning. FIG. 2A shows GUI 2 during a first step of guiding the user and illustrates a suggested action of selecting an icon to cause a change in size of a virtual implant. In other embodiments, the suggested action can be selecting an icon to cause a change in type of a virtual implant, such as femoral component 4 or tibial component 6. Specifically, the user is guided in FIG. 2A to select box 28, which has distinguishing characteristics of an outline and a guiding arrow 14. Selecting box 28 decreases the size of the femoral component 4. As can be seen in FIG. 2B, the femur size has been decreased from 6w (FIG. 2A) to 6N (FIG. 2B). In FIG. 2B, the user is guided to select icon 12*j*, which causes information related to over/under hang of femoral component 4 and tibial component 6 to appear in the form of outlines 30 (FIG. 2C). The user can therefore see how changing the size of femoral component 4 caused femoral overhang (a criterion shown in list 8 that had an unacceptable value in FIG. 2A) to have an acceptable value (as shown by the indicator 10*a* corresponding to femoral overhang in FIGS. 2B and 2C). The outline 30 associated with femoral component 4 in FIG. 2C shows the user that femoral component 4 is within the outline 30 in the medial and lateral directions. The user can use the outline 30 to evaluate whether he or she agrees with the suggested implant size. FIG. 2C also includes a completion icon 26 to demonstrate the completion of user guidance.

As in the first exemplary embodiment, although the user's actions (e.g., selecting box 28 to decrease the size of femoral component 4) in the embodiment of FIGS. 2A-2C are guided in a predetermined manner, the user has the option during each step of the process to adjust the initial surgical plan. For example, in the step shown by the GUI 2 in FIG. 2A, the user could alternatively decide to shift the femoral component 4 in different directions to eliminate femoral overhang instead of making the femoral component 4 smaller. Alternatively, the user could decide that the amount of femoral overhang shown in the step of FIG. 2A is acceptable and decide not to adjust the placement or size of femoral component 4. One of these alternative decisions by the user (e.g., any decision other than following the suggested action of decreasing the size of femoral component 4) would result in a final plan that is different from the initial surgical plan. In other words, the user is able to customize the initial surgical plan by deciding to take actions different from those suggested by the GUI 2.

Figure 3A:
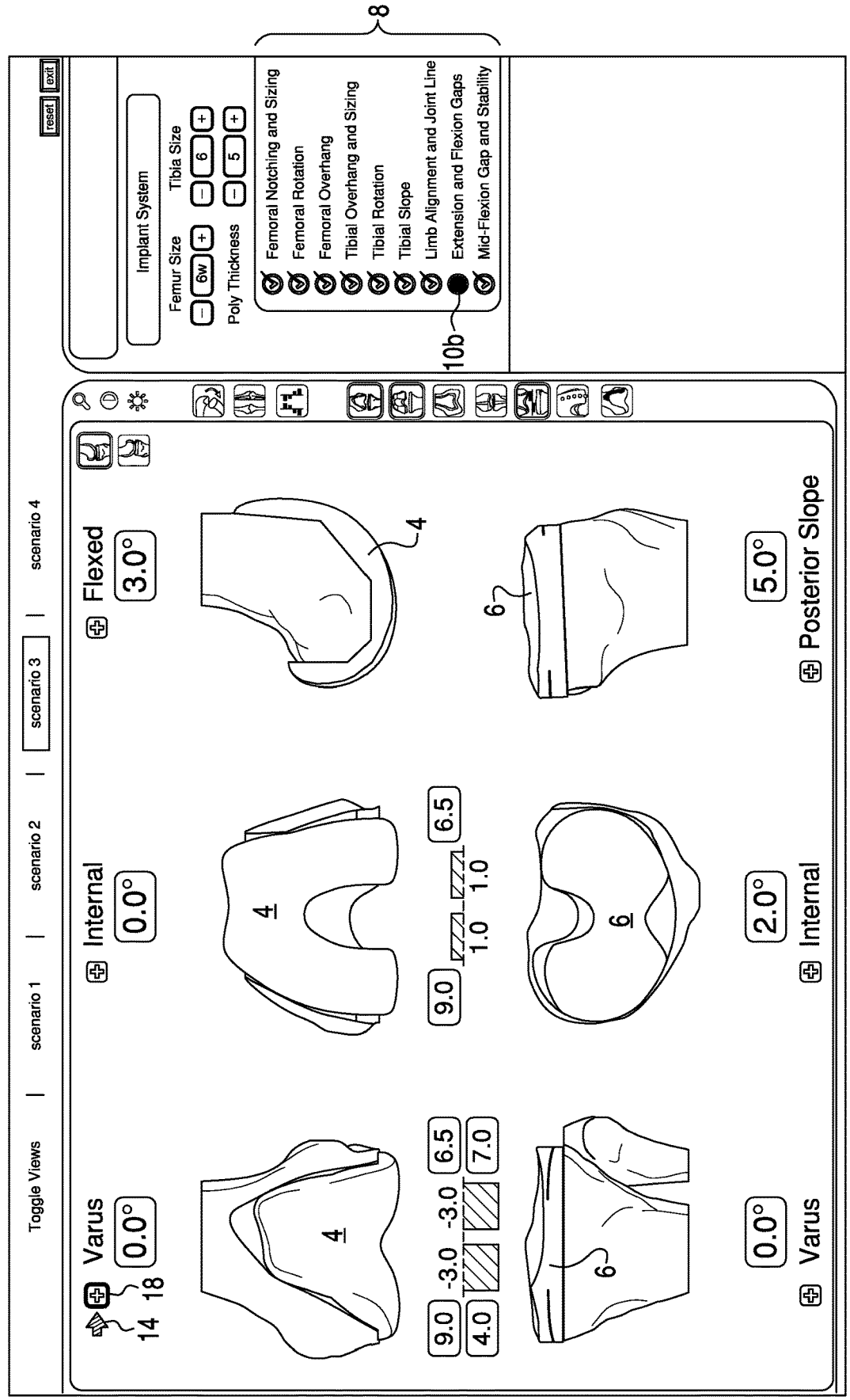
FIG. 3A is a representation of a display screen during a first step of guiding a user during surgical planning according to a third exemplary embodiment.

FIGS. 3A-3G illustrate a third exemplary embodiment for guiding a user during surgical planning. Referring to FIG. 3A, an indicator 10*b* having a second display feature corresponds to the extension and flexion gaps criterion, indicating that this criterion does not have an acceptable value. In other embodiments, the indicator may change color to indicate whether the associated criterion is acceptable or use other ways of indicating the same to the user. The exemplary embodiment of FIGS. 3A-3G leads the user through steps to adjust the femoral component 4 and tibial component 6 in a manner that will bring the extension and flexion gaps criterion to an acceptable value.

Figure 3B:
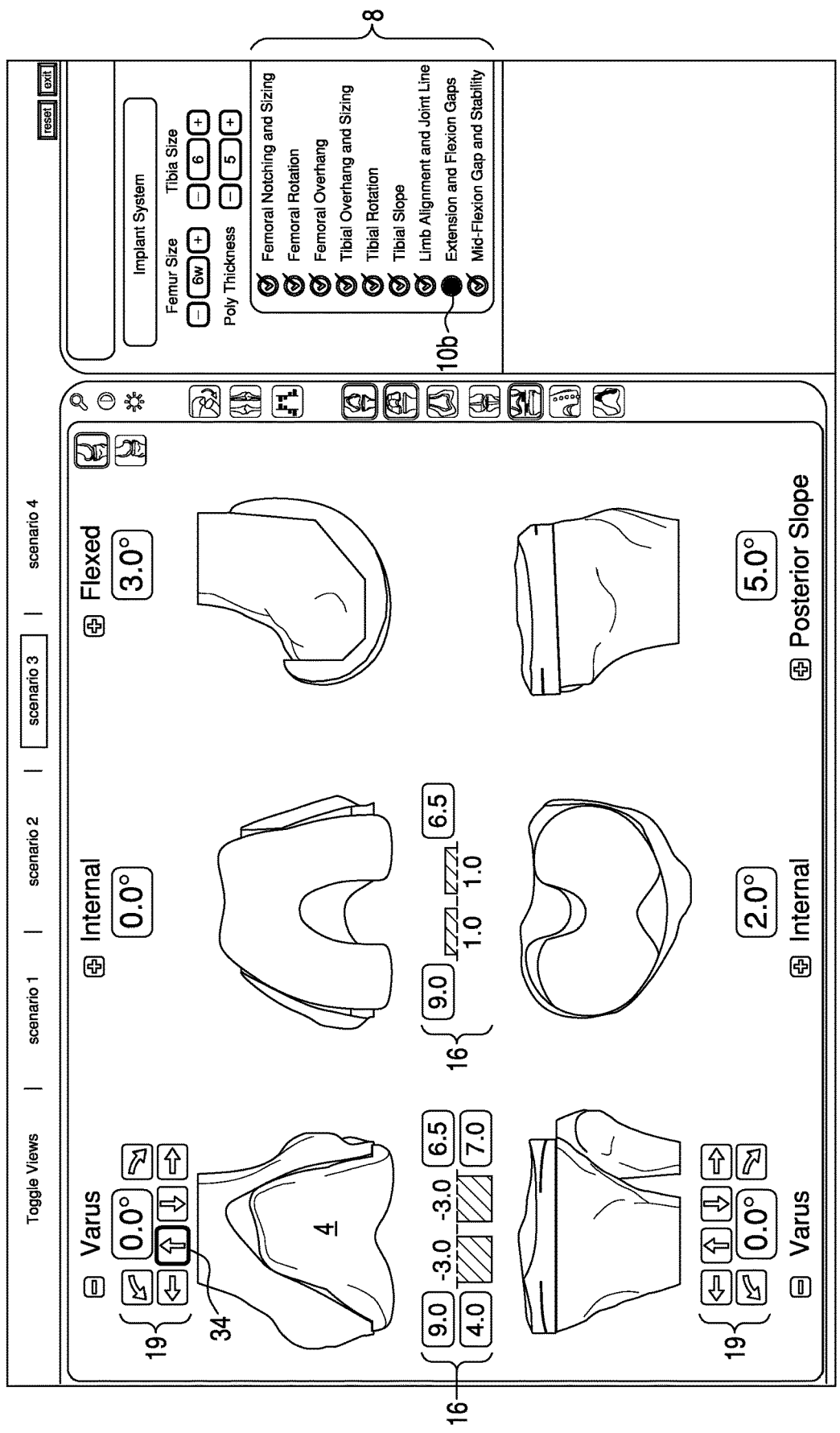
FIG. 3B is a representation of a display screen during a second step of guiding a user during surgical planning according to the third exemplary embodiment.

Referring again to FIG. 3A, expansion box 18 includes distinguishing characteristics of both an outline and a guiding arrow 14 to guide the user to select (e.g., touch, click on, etc.) expansion box 18. When the user selects expansion box 18, placement arrows 19 appear (as shown in FIG. 3B) that will allow the user to adjust the placement of femoral component 4. The marked arrow 34 includes a distinguishing characteristic to guide the user to select the marked arrow 34. When the user selects the marked arrow 34, the placement of femoral component 4 shifts upward to the placement shown in FIG. 3C. Correspondingly, measurements related to gaps between femoral component 4 and tibial component 6 are altered, as shown by the bar graphs 16, and the extension and flexion gaps criterion now has an acceptable value (see FIG. 3C). However, the limb alignment and joint line criterion now has an indicator 10*c* having a third display feature, communicating to the user that the limb alignment and joint line criterion no longer has an acceptable value, but is within predetermined ranges of an acceptable value. The user will next be guided to make adjustments that will bring the limb alignment and joint line criterion to an acceptable value.

Figure 3C:
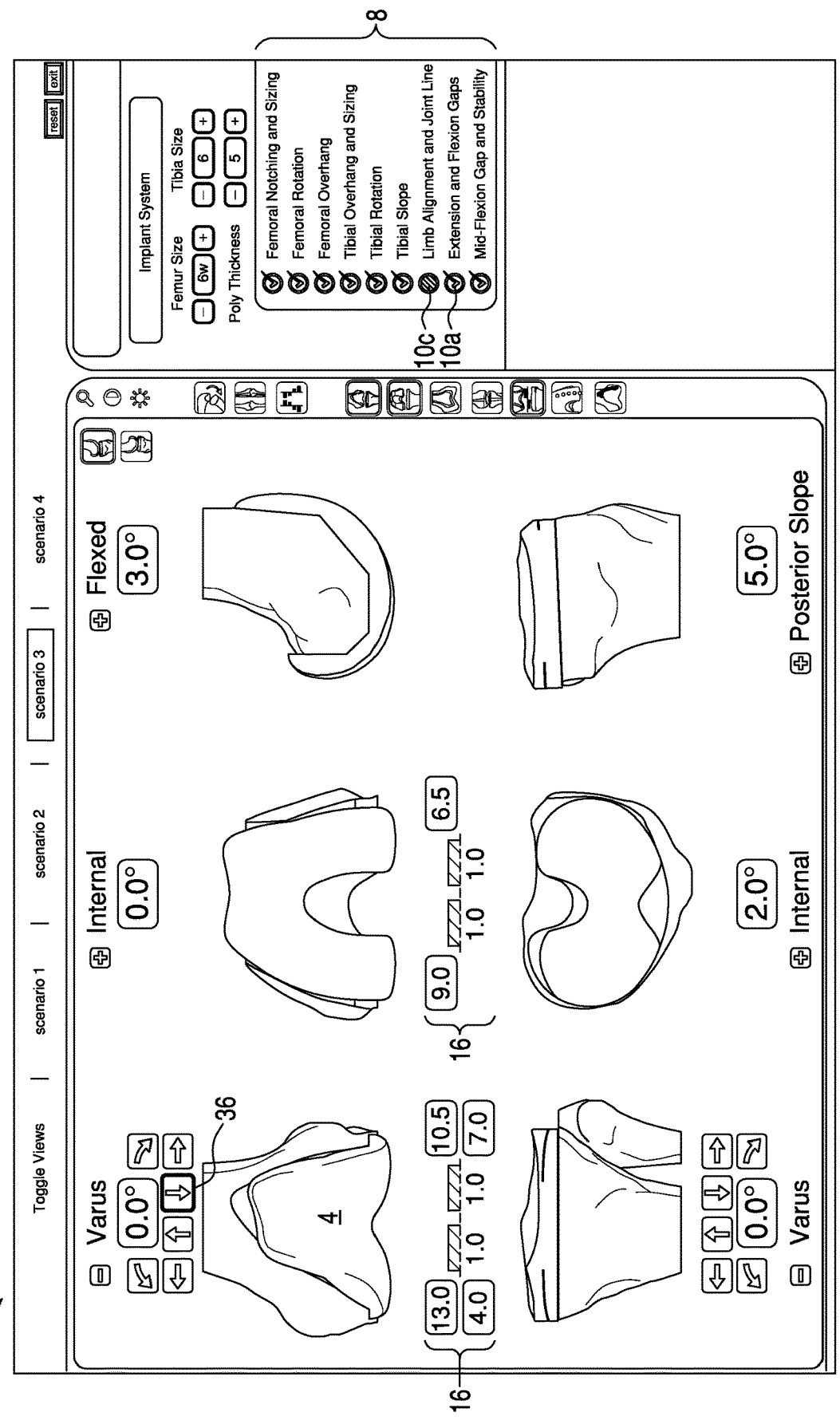
FIG. 3C is a representation of a display screen during a third step of guiding a user during surgical planning according to the third exemplary embodiment.
Figure 3D:
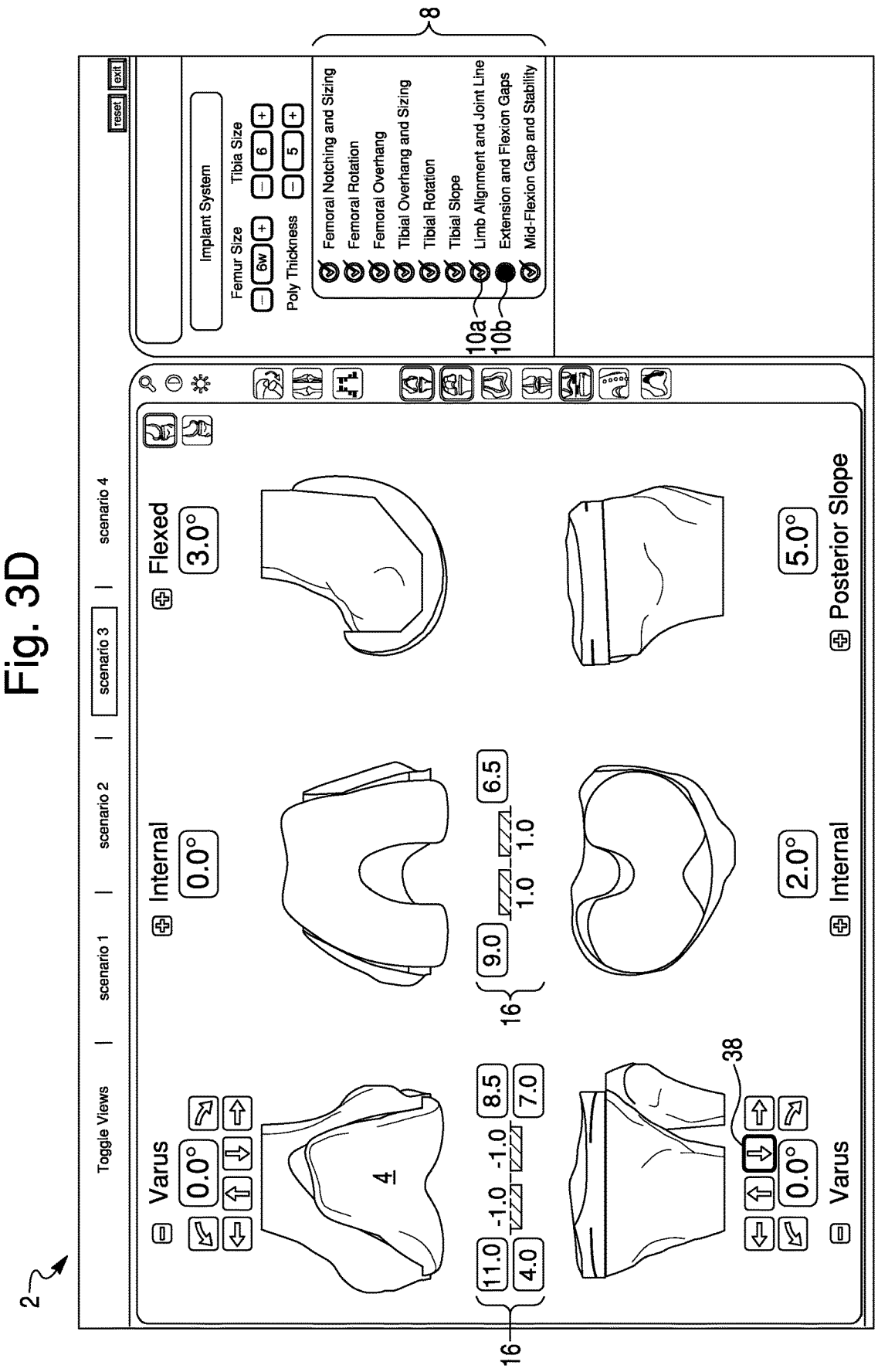
FIG. 3D is a representation of a display screen during a fourth step of guiding a user during surgical planning according to the third exemplary embodiment.

Accordingly, in FIG. 3C, the user is guided to select marked arrow 36, which shifts the femoral component 4 downward. As shown in FIG. 3D, the bar graphs 16 indicate a corresponding change in the gaps between femoral component 4 and tibial component 6. The limb alignment and joint line criterion is now at an acceptable value, as shown by the corresponding indicator 10*a*, but the extension and flexion gaps criterion is no longer at an acceptable value, as shown by the corresponding indicator 10*b*. Therefore, the planning system will guide the user to make adjustments that will bring the extension and flexion gaps criterion to an acceptable value. Accordingly, the user is guided in FIG. 3D to select marked arrow 38. Selecting marked arrow 38 causes the tibial component 6 to move downward to the position shown in FIG. 3E. The indicator corresponding to the extension and flexion gaps criterion changes from an indicator 10*b* having a second display feature to an indicator 10*a* having a third display feature to indicate to the user that the previous action (adjusting the tibial component 6) has brought the extension and flexion gaps criterion closer to an acceptable value.

Figure 3F:
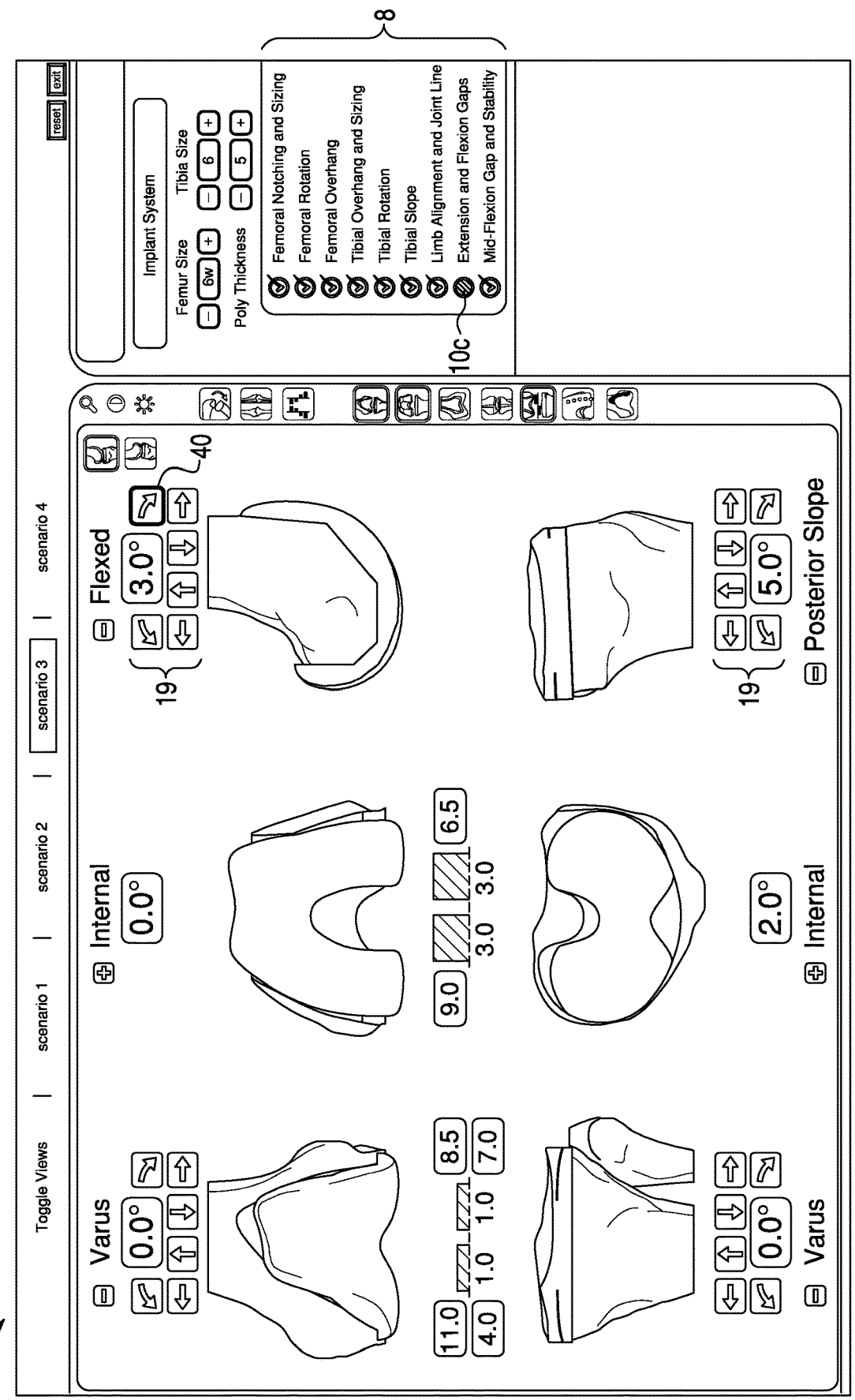
FIG. 3F is a representation of a display screen during a sixth step of guiding a user during surgical planning according to the third exemplary embodiment.

FIG. 3E guides the user to select expansion box 18, which causes additional placement arrows 19 to appear, as shown in FIG. 3F. In FIG. 3F, the user is guided to select marked arrow 40, which rotates the femoral component 4 to the placement shown in FIG. 3G. This adjustment of femoral component 4 causes the extension and flexion gaps criterion to have an acceptable value, as indicated by the checked indicator 10*a* corresponding to the extension and flexion gaps criterion. In addition, FIG. 3G includes a completion icon 26.

Figure 4A:
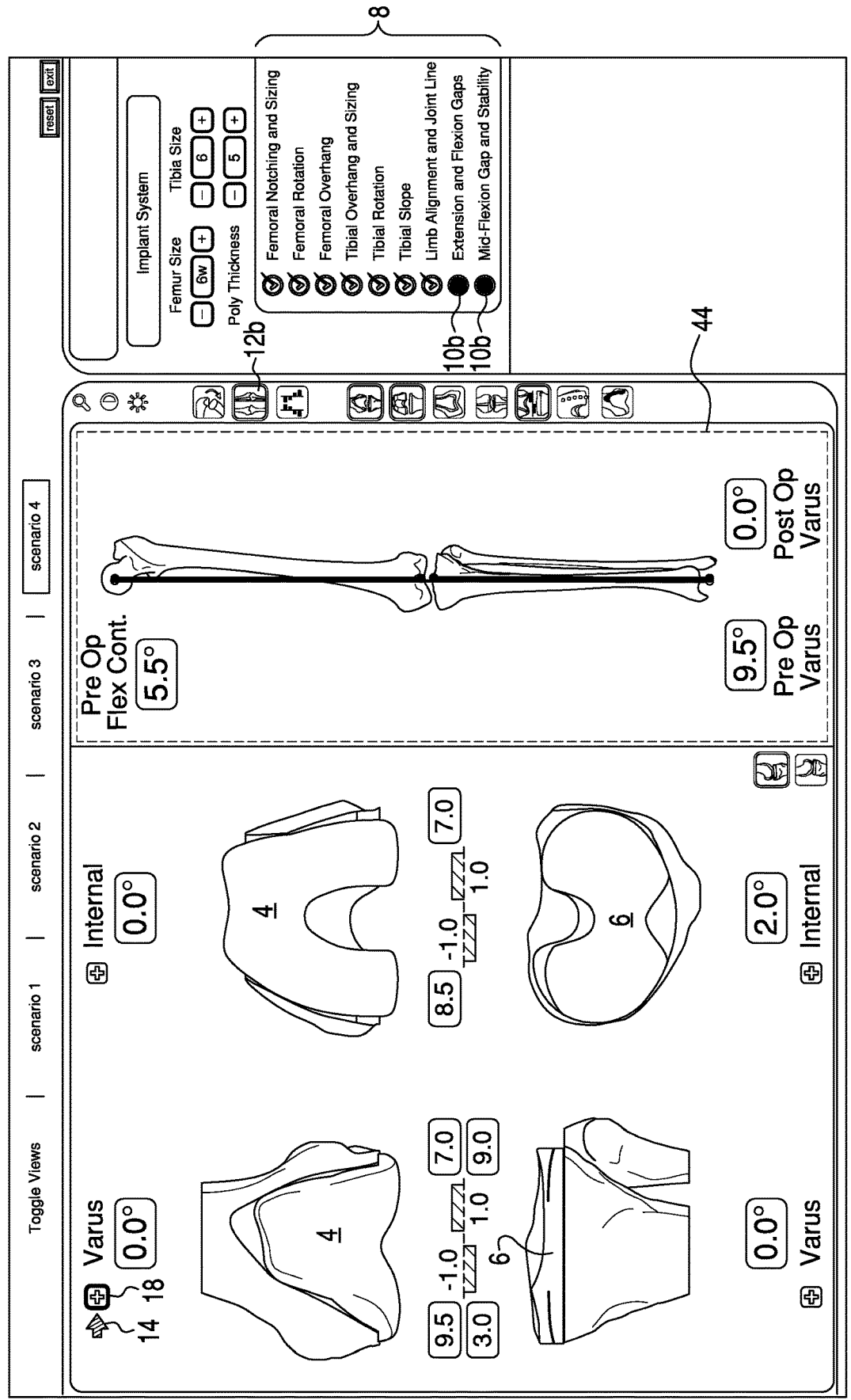
FIG. 4A is a representation of a display screen during a first step of guiding a user during surgical planning according to a fourth exemplary embodiment.

FIGS. 4A-4F illustrate a fourth exemplary embodiment for guiding a user during surgical planning. Referring to FIG. 4A, list 8 indicates that the extension and flexion gaps criterion and the mid flexion gap and stability criterion do not have acceptable values. Therefore, the embodiment of FIGS. 4A-4F will guide the user to adjust the femoral component 4 and tibial component 6 in a manner that will bring the criteria in list 8 to acceptable (or close to acceptable) values.

Figure 4B:
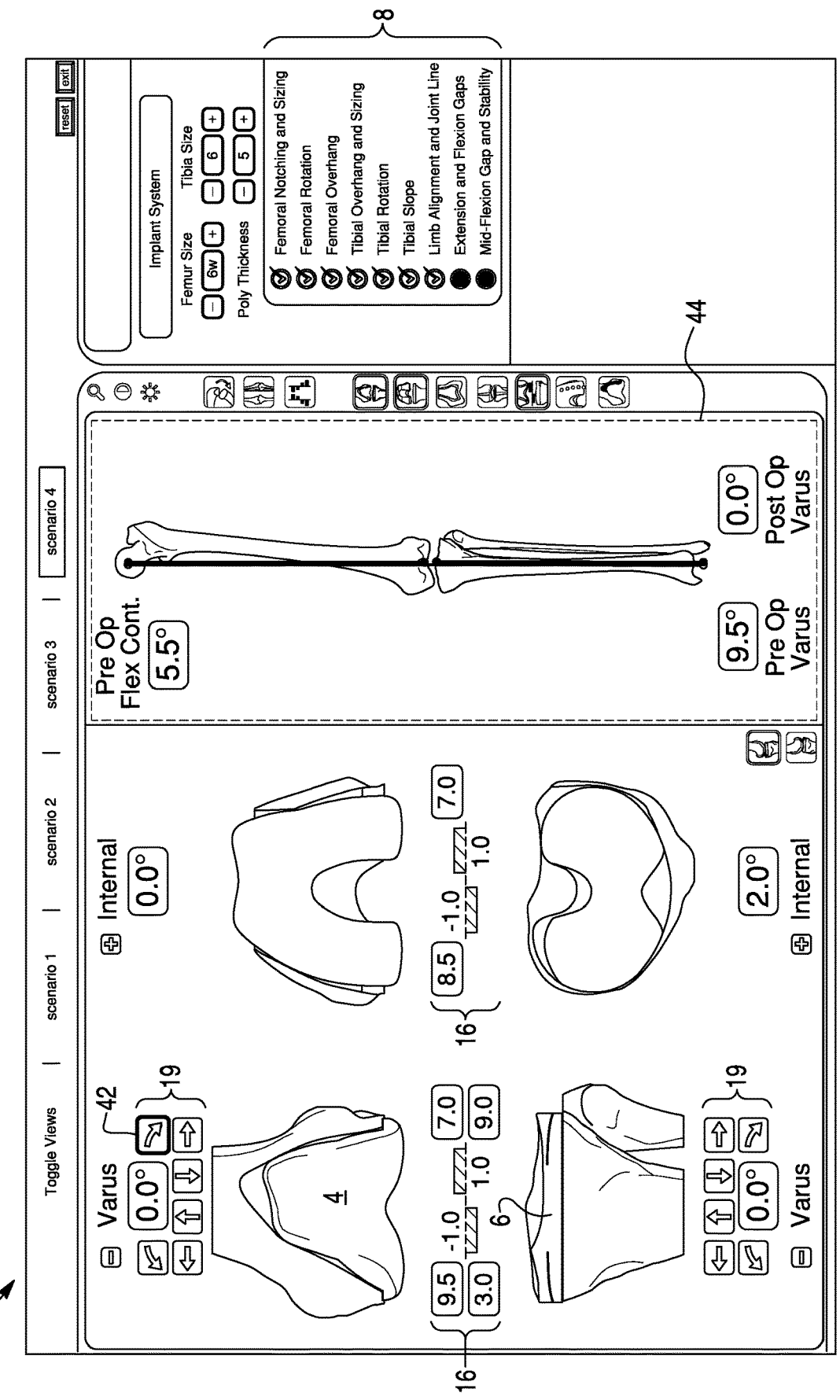
FIG. 4B is a representation of a display screen during a second step of guiding a user during surgical planning according to the fourth exemplary embodiment.
Figure 4C:
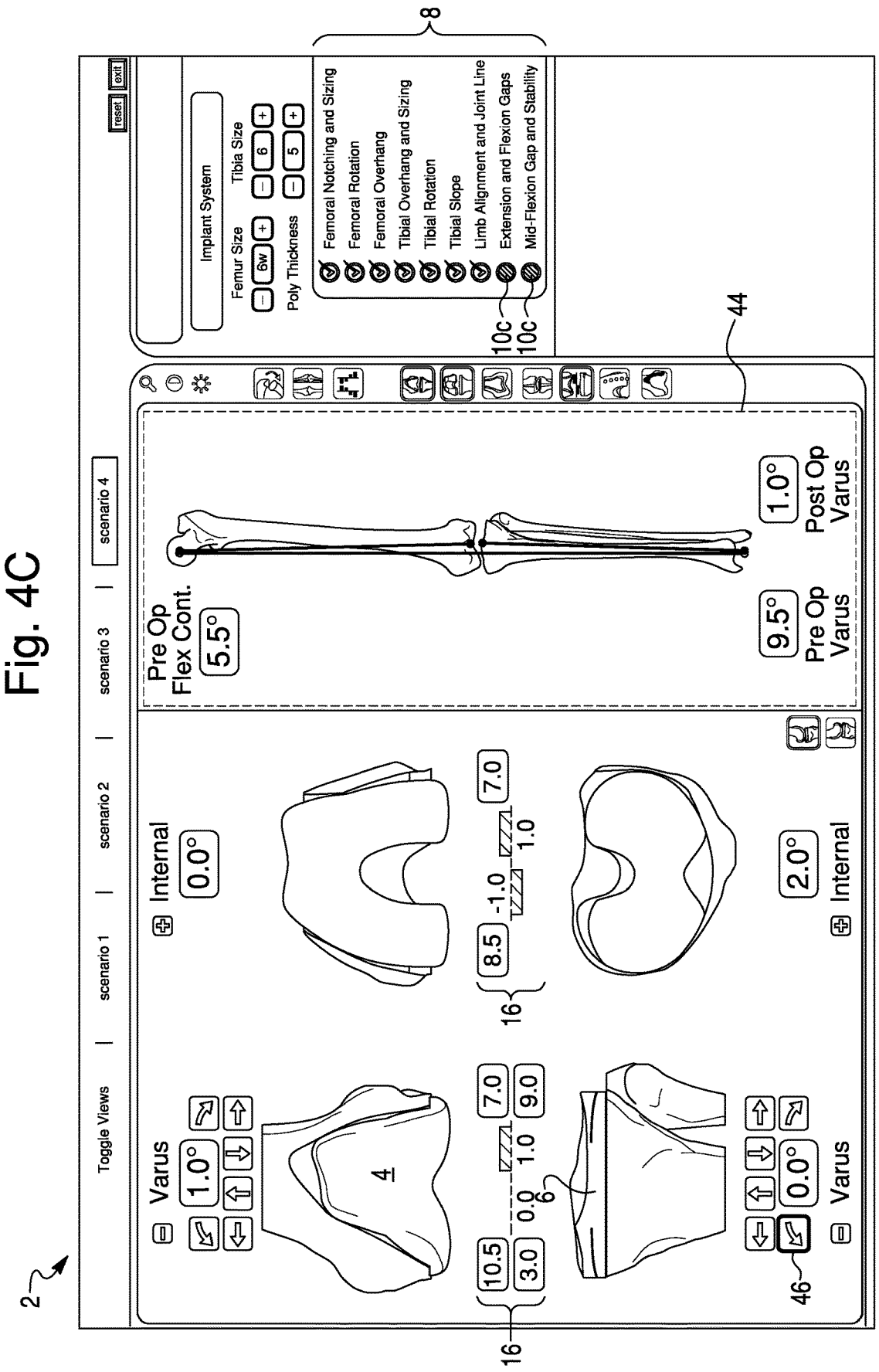
FIG. 4C is a representation of a display screen during a third step of guiding a user during surgical planning according to the fourth exemplary embodiment.

In FIG. 4A, icon 12*b* has been selected to display information related to limb alignment in the form of a diagram 44. The user is guided in FIG. 4A to select expansion box 18, which includes the distinguishing features of an outline and a guiding arrow 14. Selecting expansion box 18 causes placement arrows 19 to appear, as shown in FIG. 4B. In FIG. 4B, the user is guided to select marked arrow 42. Selecting marked arrow 42 rotates femoral component 4 from the placement shown in FIG. 4B to the placement shown in FIG. 4C. Correspondingly, the measurements related to gaps between femoral component 4 and tibial component 6 are altered, as shown by the bar graphs 16, and the femoral varus angle has been altered (e.g., from 0.0° to 1.0°). Diagram 44 also illustrates the change in limb alignment between FIG. 4B and FIG. 4C. In FIG. 4C, the extension and flexion gaps criterion and the mid flexion gap and stability criterion are marked with indicators 10*c* having a third display feature, communicating to the user that these criteria are moving closer to acceptable values. The planning system will then guide the user to make adjustments to bring all criteria to acceptable values.

Figure 4D:
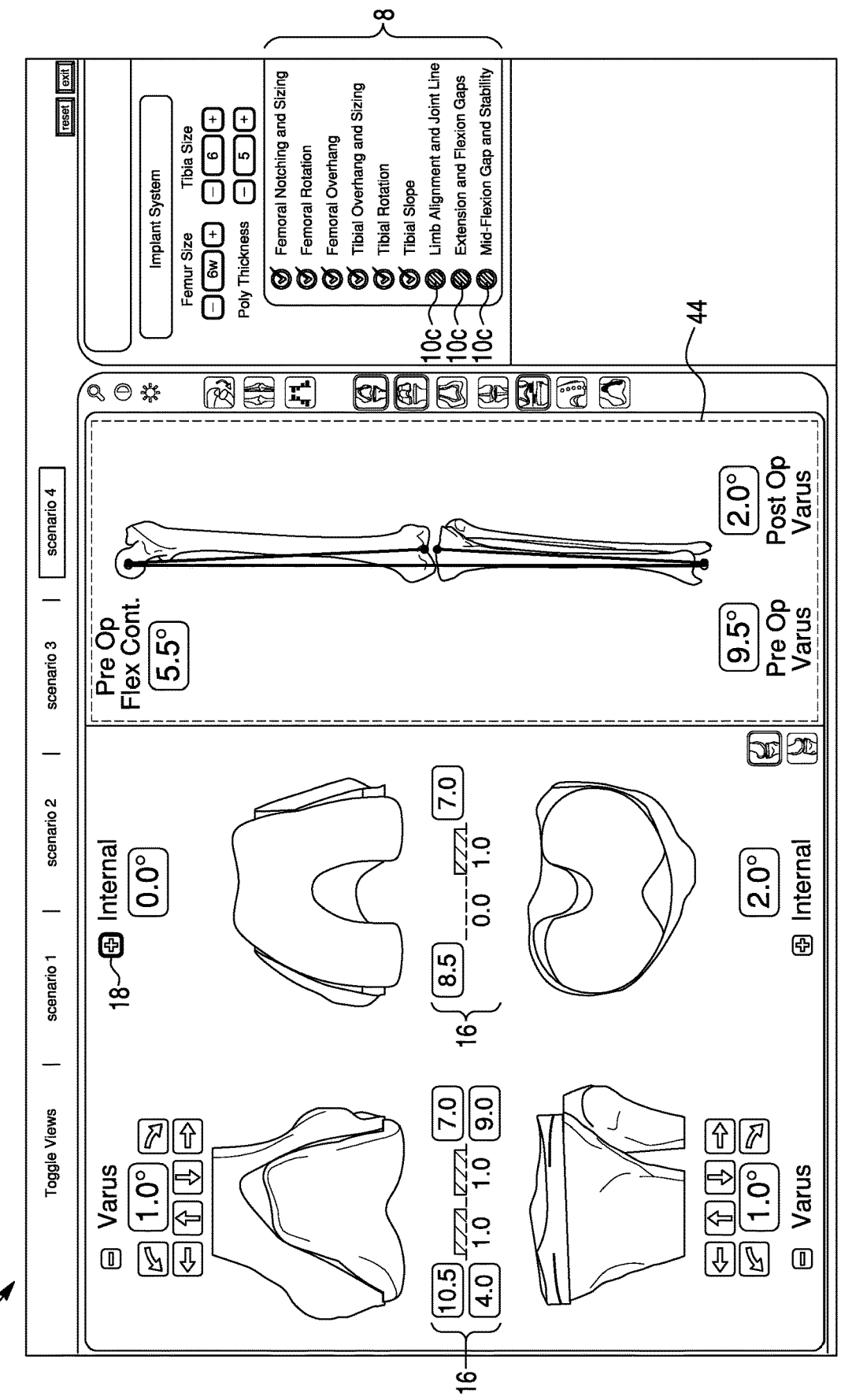
FIG. 4D is a representation of a display screen during a fourth step of guiding a user during surgical planning according to the fourth exemplary embodiment.

Accordingly, in FIG. 4C, the planning system guides the user to select marked arrow 46. Selecting marked arrow 46 rotates tibial component 6 from the placement shown in FIG. 4C to the placement shown in FIG. 4D (e.g., incrementally depending upon the number of times marked arrow 46 is selected). Correspondingly, the measurements related to gaps between femoral component 4 and tibial component 6 are altered, as shown by the bar graphs 16, and the tibial varus angle has been altered (e.g., from 0.0° to 1.0°). Diagram 44 illustrates the further change in limb alignment. In FIG. 4D, the extension and flexion gaps criterion and the mid flexion gap and stability criterion continue to be marked with indicators 10c, showing that the criteria are close, but are not yet at acceptable values. Furthermore, the limb alignment and joint line criterion is now also marked with an indicator 10c having a third display feature. Therefore, in FIG. 4D, the user is guided to select expansion arrow 18 in order to allow the user to again adjust the placement of femoral component 4. Selecting expansion box 18 causes additional placement arrows 19 to appear as shown in FIG. 4E.

Figure 4E:
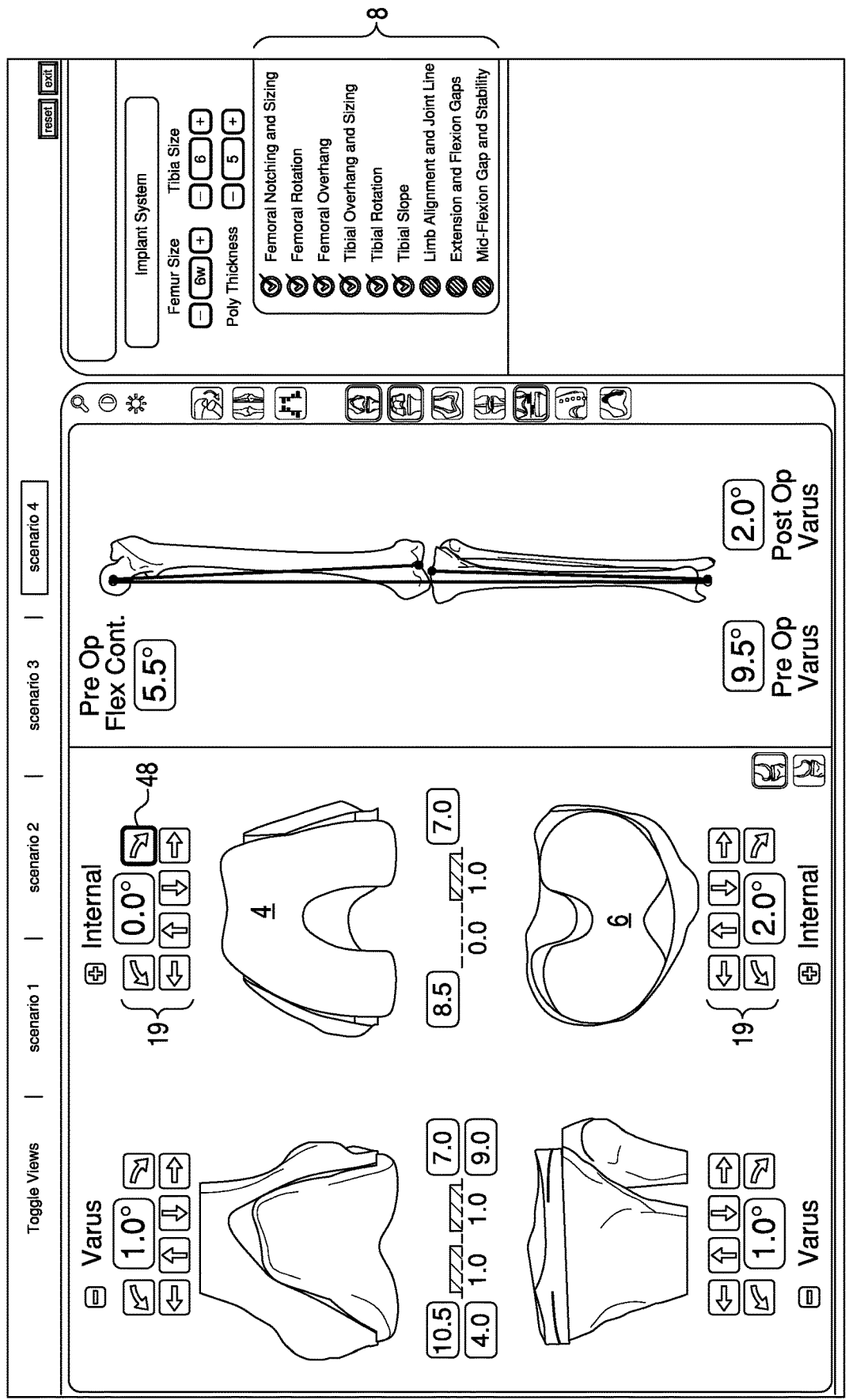
FIG. 4E is a representation of a display screen during a fifth step of guiding a user during surgical planning according to the fourth exemplary embodiment.
Figure 4F:
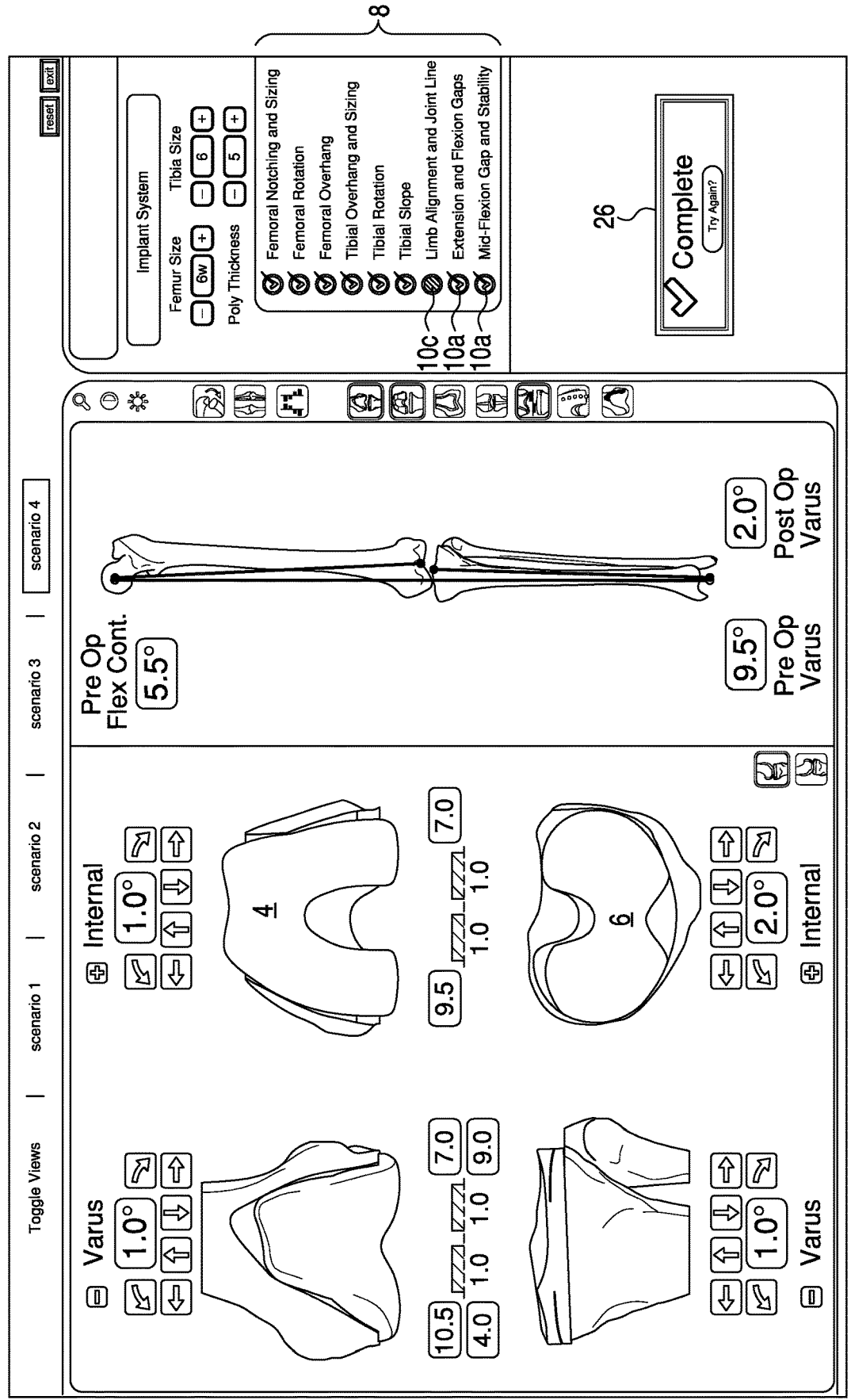
FIG. 4F is a representation of a display screen after completion of guiding a user during surgical planning according to the fourth exemplary embodiment.

In FIG. 4E, the user is guided to select marked arrow 48, which rotates the femoral component 4 from the placement shown in FIG. 4E to the placement shown in FIG. 4F. In FIG. 4F, the extension and flexion gaps criterion and the mid flexion gap and stability criterion are at acceptable values, as shown by the corresponding indicators 10a having a first display feature (e.g., being checked). However, the limb alignment and joint line criterion continues to have a corresponding indicator 10c having the third display feature showing that the criterion is close, but not yet at the desired value. Nonetheless, the planning system has arrived at the initial surgical plan created based on the input information, and FIG. 4F therefore displays a completion icon 26.

In some conventional surgical planning systems, a surgical plan is created based on input information. The user is then provided with the surgical plan without having insight into the algorithm used by the planning system to develop the surgical plan. In each of the exemplary embodiments described herein, a planning system creates an initial surgical plan based on certain input information. However, in contrast to other conventional systems, the methods described herein guide the user through a series of steps, via GUI 2, to lead the user to the initial surgical plan. The algorithm used by the planning system therefore becomes transparent to the user, and the user can easily see how the planning system arrived at the initial surgical plan.

This transparency provides users with the opportunity to customize the initial surgical plan in a straightforward manner. A user might desire to customize the surgical plan for a variety of reasons. For example, the user may have additional knowledge related to the specific patient (e.g., the patient's lifestyle or other factors that may affect the outcome of the surgical procedure), which may cause the user to want to modify the surgical plan in a particular way. As another example, the user may have years of experience performing similar surgical procedures, and may wish to modify the plan in a manner that he or she knows will lead to a more successful outcome. The methods described herein allow a user to more readily determine how to implement customizations by providing the user with awareness of the series of steps taken by the planning system, as well as providing the user with an opportunity to modify the surgical plan at each step.

Another advantage of the methods described herein relative to other planning systems is an improved user "buy in." In conventional planning systems and methods, a user is simply provided with a solution (e.g., a surgical plan) and is not aware of how the system arrived at the solution. However, when a user is taken step-by-step through the process of arriving at an initial surgical plan, as described herein, the user is able to understand the algorithm relied on by the planning system. For example, when a user is guided according to the embodiment of FIGS. 2A-2C, the user will understand that the initial surgical plan includes a femoral component 4 with a size of "6N" in order to obtain an acceptable value for femoral overhang. Similarly, when a user is guided according to the embodiment of FIGS. 3A-3G, the user will understand that the femoral component 4 and tibial component 6 are placed to ensure acceptable values for the extension and flexion gaps criterion (as well as the other criteria in list 8). Because the user is provided with more knowledge regarding the algorithm applied by the surgical planning system, the user may be more comfortable relying on and implementing the surgical plan provided by the planning system.

Another advantage of the planning systems and methods described herein is the ability to improve the algorithm applied to input information over time by analysis of user input. User input may include, for example, any user actions, such as input of information or modifications or customizations to a surgical plan, taken in connection with surgical planning as described herein. The planning systems can store data related to this user input, which can later be accessed to improve the planning system's algorithm. For example, in the exemplary embodiment of FIGS. 1A-1F, a certain placement of femoral component 4 is suggested by the planning system to achieve the initial surgical plan illustrated in FIG. 1F. However, if it is found that users typically modify the suggested femoral placement for patients with a certain type of bone structure, the algorithm might be altered to arrive automatically at the modified femoral placement when creating initial surgical plans in the future. In this manner, data obtained by evaluating user customizations can be applied to improve the planning system's algorithm.

Figure 5:
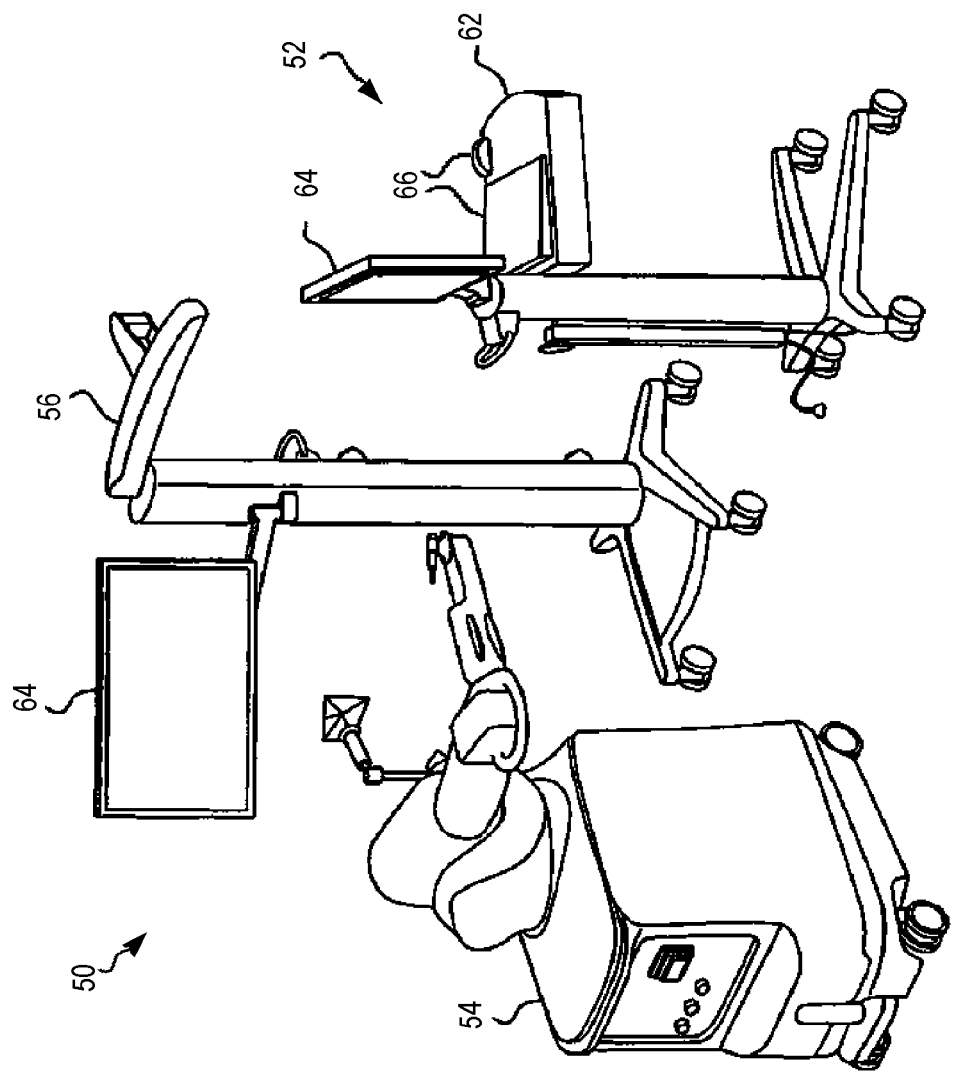
FIG. 5 is a perspective view of an embodiment of a surgical system according to an exemplary embodiment.

The methods of guiding a user during surgical planning described herein may be implemented using a treatment planning computing system, such as the computing system associated with a RIO® Robotic Arm Interactive Orthopedic System available from MAKO Surgical Corp., Ft. Lauderdale, Fla. FIG. 5 shows an embodiment of an exemplary surgical system 50 in which and for which the techniques described above can be implemented. The surgical system 50 includes a computing system 52, a haptic device 54, and a tracking system 56. In operation, the surgical system 50 enables comprehensive, intraoperative surgical planning. The surgical system 50 may also provide haptic guidance to a user (e.g., a surgeon) and/or limits the user's manipulation of the haptic device 54 as the user performs a surgical procedure.

Embodiments of the subject matter, the methods, and the operations described in this specification can be implemented in digital electronic circuitry, or in computer software embodied on a tangible medium, firmware, or hardware, including the structures disclosed in this specification and their structural equivalents, or in combinations of one or more of them. In the embodiment of FIG. 5, the computing system 52 may include hardware and software for operation and control of the surgical system 50. Such hardware and/or software is configured to enable the system 50 to perform the techniques described herein. The computing system 52 includes a surgical controller 62, a display device 64, and an input device 66.

The surgical controller 62 may be any known computing system but is preferably a programmable, processor-based system. For example, the surgical controller 62 may include a microprocessor, a hard drive, random access memory (RAM), read only memory (ROM), input/output (I/O) circuitry, and any other known computer component. The surgical controller 62 is preferably adapted for use with various types of storage devices (persistent and removable), such as, for example, a portable drive, magnetic storage, solid state storage (e.g., a flash memory card), optical storage, and/or network/Internet storage. The surgical controller 62 may comprise one or more computers, including, for example, a personal computer or a workstation operating under a suitable operating system and preferably includes a graphical user interface (GUI).

Figure 6:
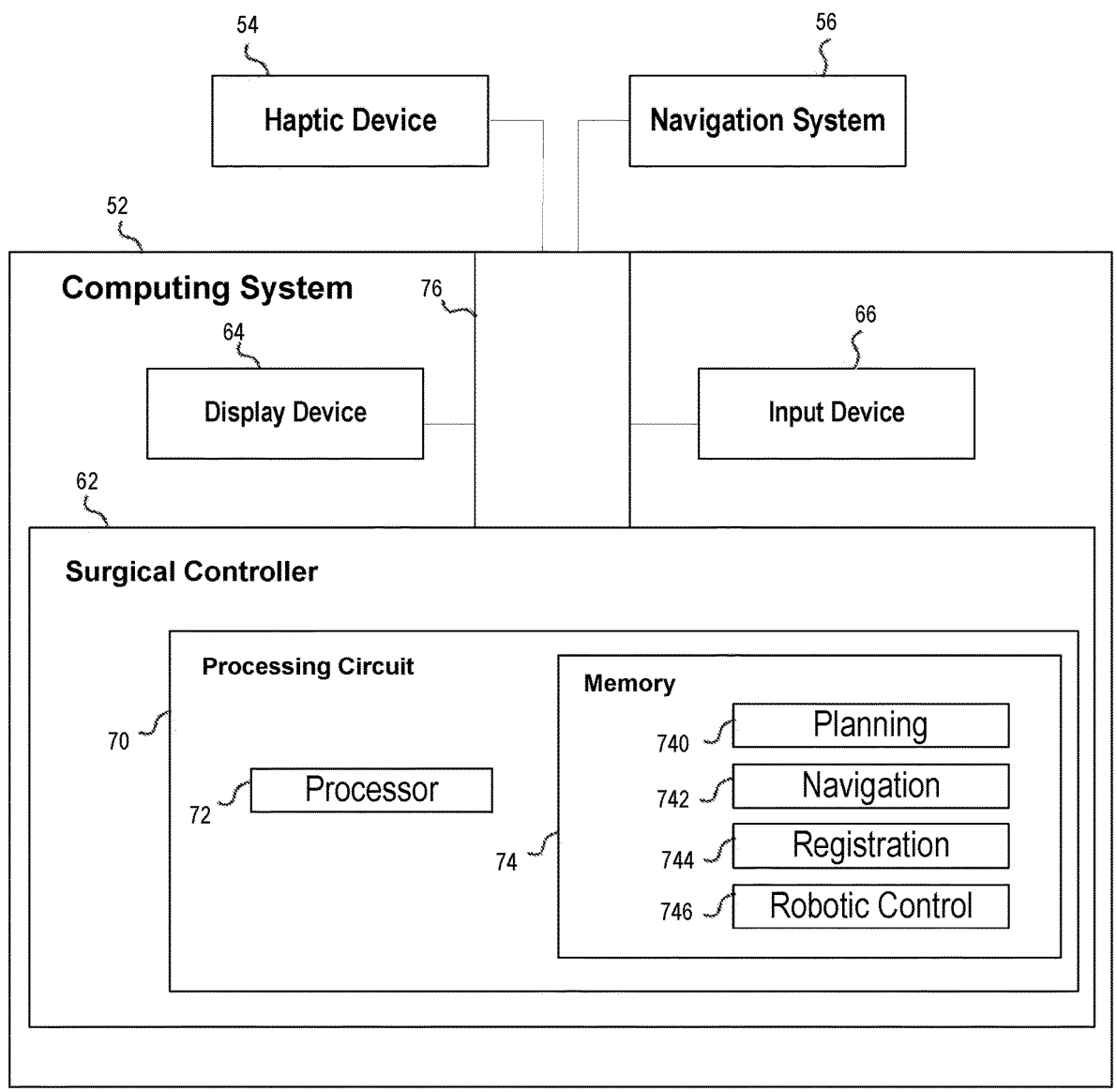
FIG. 6 is a block diagram of a model surgical system according to an exemplary embodiment.

Referring to FIG. 6, in an exemplary embodiment, the surgical controller 62 includes a processing circuit 70 having a processor 72 and memory 74. Processor 72 can be implemented as a general purpose processor executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit), a group of processing components, or other suitable electronic processing components. Generally, a processor will receive instructions and data from a read only memory or a random access memory or both. Memory 74 (e.g., memory, memory unit, storage device, etc.) comprises one or more devices (e.g., RAM, ROM, Flash-memory, hard disk storage, etc.) for storing data and/or computer code for completing or facilitating the various processes described in the present application. Memory 74 may be or include volatile memory or non-volatile memory. Memory 74 may include database components, object code components, script components, or any other type of information structure for supporting the various activities described in the present application. According to an exemplary embodiment, memory 74 is communicably connected to processor 72 and includes computer code for executing one or more processes described herein. The memory 74 may contain a variety of modules, each capable of storing data and/or computer code related to specific types of functions. In one embodiment, memory 74 contains several modules related to surgical procedures, such as a planning module 740, a navigation module 742, a registration module 744, and a robotic control module 746.

Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). Accordingly, the computer storage medium may be tangible and non-transitory.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an embodiment of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Referring to the embodiment of surgical system 50 depicted in FIG. 6, the surgical controller 62 further includes a communication interface 76. The communication interface 76 of the computing system 52 is coupled to a computing device (not shown) of the haptic device 54 via an interface and to the tracking system 56 via an interface. The interfaces can include a physical interface and a software interface. The physical interface of the communication interface 76 can be or include wired or wireless interfaces (e.g., jacks, antennas, transmitters, receivers, transceivers, wire terminals, etc.) for conducting data communications with external sources via a direct connection or a network connection (e.g., an Internet connection, a LAN, WAN, or WLAN connection, etc.). The software interface may be resident on the surgical controller 62, the computing device (not shown) of the haptic device 54, and/or the tracking system 56. In some embodiments, the surgical controller 62 and the computing device (not shown) are the same computing device.

The software may also operate on a remote server, housed in the same building as the surgical system 50, or at an external server site.

Computer system 52 also includes display device 64. The display device 64 is a visual interface between the computing system 52 and the user. GUI 2 described according to the exemplary embodiments of FIGS. 1A-4F may be displayed on display device 64. The display device 64 is connected to the surgical controller 62 and may be any device suitable for displaying text, images, graphics, and/or other visual output. For example, the display device 64 may include a standard display screen (e.g., LCD, CRT, OLED, TFT, plasma, etc.), a touch screen, a wearable display (e.g., eyewear such as glasses or goggles), a projection display, a head-mounted display, a holographic display, and/or any other visual output device. The display device 64 may be disposed on or near the surgical controller 62 (e.g., on the cart as shown in FIG. 5) or may be remote from the surgical controller 62 (e.g., mounted on a stand with the tracking system 56). The display device 64 is preferably adjustable so that the user can position/reposition the display device 64 as needed during a surgical procedure. For example, the display device 64 may be disposed on an adjustable arm (not shown) or to any other location well-suited for ease of viewing by the user. As shown in FIG. 5 there may be more than one display device 64 in the surgical system 50.

The display device 64 may be used to display any information useful for a medical procedure, such as, for example, images of anatomy generated from an image data set obtained using conventional imaging techniques, graphical models (e.g., CAD models of implants, instruments, anatomy, etc.), graphical representations of a tracked object (e.g., anatomy, tools, implants, etc.), constraint data (e.g., axes, articular surfaces, etc.), representations of implant components, digital or video images, registration information, calibration information, patient data, user data, measurement data, software menus, selection buttons, status information, and the like.

In addition to the display device 64, the computing system 52 may include an acoustic device (not shown) for providing audible feedback to the user. The acoustic device is connected to the surgical controller 62 and may be any known device for producing sound. For example, the acoustic device may comprise speakers and a sound card, a motherboard with integrated audio support, and/or an external sound controller. In operation, the acoustic device may be adapted to convey information to the user. For example, the surgical controller 62 may be programmed to signal the acoustic device to produce a sound, such as a voice synthesized verbal indication "DONE," to indicate that a step of a surgical procedure is complete. Similarly, the acoustic device may be used to alert the user to a sensitive condition, such as producing a tone to indicate that a surgical cutting tool is nearing a critical portion of soft tissue.

To provide for other interaction with a user, embodiments of the subject matter described in this specification can be implemented on a computer having input device 66 that enables the user to communicate with the surgical system 50. The input device 66 is connected to the surgical controller 62 and may include any device enabling a user to provide input to a computer. For example, the input device 66 can be a known input device, such as a keyboard, a mouse, a trackball, a touch screen, a touch pad, voice recognition hardware, dials, switches, buttons, a trackable probe, a foot pedal, a remote control device, a scanner, a camera, a microphone, and/or a joystick. For example, input device 66 can allow the user to make the selections as described above to adjust the surgical plan. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The system 50 also includes a tracking (or localizing) system 56 that is configured to determine a pose (i.e., position and orientation) of one or more objects during a surgical procedure to detect movement of the object(s). For example, the tracking system 56 may include a detection device that obtains a pose of an object with respect to a coordinate frame of reference of the detection device. As the object moves in the coordinate frame of reference, the detection device tracks the pose of the object to detect (or enable the surgical system 50 to determine) movement of the object. As a result, the computing system 52 can capture data in response to movement of the tracked object or objects. Tracked objects may include, for example, tools/instruments, patient anatomy, implants/prosthetic devices, and components of the surgical system 50. Using pose data from the tracking system 56, the surgical system 50 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the surgical controller 62 and/or the computer device of the haptic device 54. For example, utilizing pose data from the tracking system 56, the surgical system 50 is able to associate the physical anatomy, such as the patient's spine, with a representation of the anatomy (such as an image displayed on the display device 64). Based on tracked object and registration data, the surgical system 50 may determine, for example, a spatial relationship between the image of the anatomy and the relevant anatomy.

Registration may include any known registration technique, such as, for example, image-to-image registration (e.g., monomodal registration where images of the same type or modality, such as fluoroscopic images or MR images, are registered and/or multimodal registration where images of different types or modalities, such as MRI and CT, are registered); image-to-physical space registration (e.g., image-to-patient registration where a digital data set of a patient's anatomy obtained by conventional imaging techniques is registered with the patient's actual anatomy); and/or combined image-to-image and image-to-physical-space registration (e.g., registration of preoperative CT and MM images to an intraoperative scene). The computing system 52 may also include a coordinate transform process for mapping (or transforming) coordinates in one space to those in another to achieve spatial alignment or correspondence. For example, the surgical system 50 may use the coordinate transform process to map positions of tracked objects (e.g., patient anatomy, etc.) into a coordinate system used by a process running on the computer of the haptic device and/or the surgical controller 62. As is well known, the coordinate transform process may include any suitable transformation technique, such as, for example, rigid-body transformation, non-rigid transformation, affine transformation, and the like.

The tracking system 56 may be any tracking system that enables the surgical system 50 to continually determine (or track) a pose of the relevant anatomy of the patient. For example, the tracking system 56 may include a non-mechanical tracking system, a mechanical tracking system, or any combination of non-mechanical and mechanical tracking systems suitable for use in a surgical environment. The non-mechanical tracking system may include an optical (or visual), magnetic, radio, or acoustic tracking system. Such systems typically include a detection device adapted to locate in predefined coordinate space specially recognizable trackable elements (or trackers) that are detectable by the detection device and that are either configured to be attached to the object to be tracked or are an inherent part of the object to be tracked. For example, a trackable element may include an array of markers having a unique geometric arrangement and a known geometric relationship to the tracked object when the trackable element is attached to the tracked object. The known geometric relationship may be, for example, a predefined geometric relationship between the trackable element and an endpoint and axis of the tracked object. Thus, the detection device can recognize a particular tracked object, at least in part, from the geometry of the markers (if unique), an orientation of the axis, and a location of the endpoint within a frame of reference deduced from positions of the markers.

The markers may include any known marker, such as, for example, extrinsic markers (or fiducials) and/or intrinsic features of the tracked object. Extrinsic markers are artificial objects that are attached to the patient (e.g., markers affixed to skin, markers implanted in bone, stereotactic frames, etc.) and are designed to be visible to and accurately detectable by the detection device. Intrinsic features are salient and accurately locatable portions of the tracked object that are sufficiently defined and identifiable to function as recognizable markers (e.g., landmarks, outlines of anatomical structure, shapes, colors, or any other sufficiently recognizable visual indicator). The markers may be located using any suitable detection method, such as, for example, optical, electromagnetic, radio, or acoustic methods as are well known. For example, an optical tracking system having a stationary stereo camera pair sensitive to infrared radiation may be used to track markers that emit infrared radiation either actively (such as a light emitting diode or LED) or passively (such as a spherical marker with a surface that reflects infrared radiation). Similarly, a magnetic tracking system may include a stationary field generator that emits a spatially varying magnetic field sensed by small coils integrated into the tracked object.

The haptic device 54 may be the Tactile Guidance System™ (TGS™) manufactured by MAKO Surgical Corp., and used to prepare the surface of the patient's bone for insertion of the spinal plate 10. The haptic device 54 provides haptic (or tactile) guidance to guide the surgeon during a surgical procedure. The haptic device is an interactive surgical robotic arm that holds a surgical tool (e.g., a surgical burr) and is manipulated by the surgeon to perform a procedure on the patient, such as cutting a surface of a bone in preparation for spinal plate installation. As the surgeon manipulates the robotic arm to move the tool and sculpt the bone, the haptic device 54 guides the surgeon by providing force feedback that constrains the tool from penetrating a virtual boundary.

The construction and arrangement of the systems and methods as shown in the various exemplary embodiments are illustrative only. Although only a few embodiments have been described in detail in this disclosure, many modifications are possible. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A method for improving the development of an initial surgical plan, the method comprising:
   receiving a plurality of sets of input information;
   developing a plurality of initial surgical plans by applying a planning algorithm to the plurality of sets of input information;
   allowing a user to customize the initial surgical plans by providing input related to pre-operative modifications to the initial surgical plans, the pre-operative modifications comprising virtually repositioning virtual implants relative to bone models;
   storing information related to the pre-operative modifications to the initial surgical plans;
   improving the planning algorithm by using the stored information to generate an altered planning algorithm based on the pre-operative modifications to the initial surgical plans by the user; and
   developing a subsequent initial surgical plan using the altered planning algorithm, wherein the altered planning provides different positions of the virtual implants relative to the bone models as compared to the planning algorithm.

2. The method of claim 1, wherein the input related to the pre-operative modifications comprise rotating and translating the virtual implants relative to the bone models.

3. The method of claim 1, wherein a first initial plan of the plurality of initial surgical plans is associated with a particular anatomical structure and wherein the subsequent initial plan is developed for a different anatomical structure.

4. The method of claim 1, wherein allowing a user to customize the initial surgical plans comprises:
   guiding a user by identifying a series of suggested actions to the user on a graphical user interface, wherein if the user performs the series of suggested actions, the series of suggested actions lead the user to a first initial surgical plan of the plurality of the initial surgical plans; and
   providing the user with an option to deviate from the series of suggested actions by performing one or more non-suggested actions, wherein deviation from the series of suggested actions leads to modifications to the first initial surgical plan.

5. The method of claim 4, wherein guiding a user comprises:
   displaying a plurality of criteria, wherein each of the plurality of criteria is associated with an acceptable value pertaining to said first initial surgical plan;
   displaying a plurality of indicators, wherein each of the plurality of indicators is configured to indicate whether the acceptable value of the corresponding one of the plurality of criteria is met; and
   displaying an icon having a distinguishing characteristic configured to indicate the next suggested action to lead the user to the first initial surgical plan.

6. The method of claim 5, wherein the plurality of criteria are selected from the group consisting of: femoral notching and sizing, femoral rotation, femoral overhang, tibial overhang and sizing, tibial rotation, tibial slope, limb alignment and joint line, extension and flexion gaps, and mid flexion gap and stability.

7. The method of claim 4, wherein at least one of the suggested actions is selecting an icon to cause additional information to be displayed to the user.

8. The method of claim 4, wherein at least one of the suggested actions is selecting an icon to cause a change in placement of the virtual implant.

9. The method of claim 4, wherein at least one of the suggested actions is selecting an icon to cause a change in size of the virtual implant.

10. The method of claim 4, wherein at least one of the suggested actions is selecting an icon to cause a change in type of the virtual implant.

11. The method of claim 1, wherein developing the subsequent initial surgical plan comprises receiving a new set of input information and applying the altered planning algorithm to the new set of input information.

12. The method of claim 1, wherein applying the planning algorithm to a first set of the input information and applying the altered planning algorithm to a first set of the input information results in different initial surgical plans.

13. A system for improving the development of an initial surgical plan, comprising:
a processing circuit configured to:
receive input information;
develop an initial surgical plan by applying the input information to a planning algorithm, the initial surgical plan comprising an initial placement of a virtual implant relative to a bone model;
allow a user to customize the initial surgical plan by providing pre-operative modifications to the initial placement of the virtual implant relative to the bone model;
generate an altered planning algorithm based on the pre-operative modifications to the initial placement by the user, wherein applying the altered planning algorithm to the input information results in a different initial placement as compared to the initial placement; and
develop a subsequent initial surgical plan using the altered planning algorithm.

14. The system of claim 13, wherein the pre-operative modifications to the initial placement comprise translating and rotating a size of the virtual implant relative to the bone model.

15. The system of claim 13, wherein the initial surgical plan is associated with a particular anatomical structure and wherein the subsequent initial plan is developed for a different particular anatomical structure.

16. The system of claim 13, wherein the processing circuit is further configured to allow a user to customize the initial surgical plan by:
guiding a user by identifying a series of suggested actions to the user on a graphical user interface, wherein if the user performs the series of suggested actions, the series of suggested actions lead the user to the initial surgical plan; and
providing the user with an option to deviate from the series of suggested actions by performing one or more non-suggested actions, wherein deviation from the series of suggested actions leads to modifications to the initial surgical plan.

17. The system of claim 16, wherein the processing circuit is further configured to identify a series of suggested actions to the user by:
displaying a plurality of criteria, wherein each of the plurality of criteria is associated with an acceptable value pertaining to said initial surgical plan;
displaying a plurality of indicators, wherein each of the plurality of indicators is configured to indicate whether the acceptable value of the corresponding one of the plurality of criteria is met; and
displaying an icon having a distinguishing characteristic configured to indicate the next suggested action to lead the user to the initial surgical plan.

18. The system of claim 16, wherein the suggested actions comprise at least one of selecting an icon to cause additional information to be displayed to the user, selecting an icon to cause a change in size of the virtual implant, or selecting an icon to cause a change in type of the virtual implant.

19. The system of claim 13, wherein the processing circuit is configured to develop the subsequent initial surgical plan by receiving a new set of input information and applying the altered planning algorithm to the new set of input information.

20. The system of claim 13, wherein applying the planning algorithm to the input information and applying the altered planning algorithm to the input information results in different initial surgical plans.

* * * * *